(12) United States Patent
Shiono et al.

(10) Patent No.: US 8,017,300 B2
(45) Date of Patent: Sep. 13, 2011

(54) COMPOUND, POSITIVE RESIST COMPOSITION AND METHOD FOR FORMING RESIST PATTERN

(75) Inventors: Daiju Shiono, Kawasaki (JP); Taku Hirayama, Kawasaki (JP); Hideo Hada, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 461 days.

(21) Appl. No.: 12/299,371

(22) PCT Filed: Mar. 20, 2007

(86) PCT No.: PCT/JP2007/055661
§ 371 (c)(1),
(2), (4) Date: Nov. 3, 2008

(87) PCT Pub. No.: WO2007/148456
PCT Pub. Date: Dec. 27, 2007

(65) Prior Publication Data
US 2009/0202939 A1     Aug. 13, 2009

(30) Foreign Application Priority Data

Jun. 20, 2006   (JP) ................................. 2006-169854

(51) Int. Cl.
*G03F 7/004*   (2006.01)
*G03F 7/039*   (2006.01)
*G03F 7/20*    (2006.01)
*G03F 7/30*    (2006.01)

(52) U.S. Cl. .......... 430/270.1; 430/326; 560/81; 560/84

(58) Field of Classification Search ........................ None
See application file for complete search history.

(56) References Cited

U.S. PATENT DOCUMENTS

| | | | |
|---|---|---|---|
| 5,945,517 A | 8/1999 | Nitta et al. | |
| 6,180,313 B1 | 1/2001 | Yukawa et al. | |
| 2009/0269698 A1* | 10/2009 | Shiono et al. | 430/270.1 |

FOREIGN PATENT DOCUMENTS

| | | |
|---|---|---|
| JP | A-06-266109 | 9/1994 |
| JP | A-09-208554 | 8/1997 |
| JP | A-10-123703 | 5/1998 |
| JP | A-11-035551 | 2/1999 |
| JP | A-11-035552 | 2/1999 |
| JP | A-11-035573 | 2/1999 |
| JP | A-11-322707 | 11/1999 |
| JP | 2001-312055 A | 11/2001 |
| JP | 2006-39281 A | 2/2006 |
| JP | 2007-31402 A | 2/2007 |

(Continued)

OTHER PUBLICATIONS

Office Action issued on Taiwanese Patent Application No. 096112936, dated Feb. 9, 2011.

T. Hirayama, D. Shiono, H. Hada and J. Onodera: *New Photoresist Based on Amorphous Low Molecular Weight Polyphenols*, Journal of Photopolymer Science and Technology, v. 17, No. 3 (2004), pp. 435-440.

(Continued)

*Primary Examiner* — Sin J. Lee
(74) *Attorney, Agent, or Firm* — Knobbe Martens Olson & Bear LLP

(57) ABSTRACT

Disclosed are a compound that can be used for a resist composition, a positive resist composition that includes the compound, and a method for forming a resist pattern.

Specifically disclosed is a compound represented by a formula (A-1). In the formula (A-1), $R^{11}$ to $R^{17}$ each represents an alkyl group or an aromatic hydrocarbon group; g and j each represents an integer of 1 or greater, and k and q each represents an integer of 0 or greater, provided that g+j+k+q is not greater than 5; b represents an integer of 1 or greater, and l and m each represents an integer of 0 or greater, provided that b+l+m is not greater than 4; c represents an integer of 1 or greater, and n and o each represents an integer of 0 or greater, provided that c+n+o is not greater than 4; A represents a trivalent aromatic cyclic group, alkyl group or aliphatic cyclic group, or a trivalent organic group having an aromatic cyclic group or an aliphatic cyclic group; and Z represents a group represented by a formula (z1). In the formula (z1), Y represents an alkylene group, a divalent aromatic hydrocarbon group or aliphatic cyclic group, or a divalent organic group having an aromatic hydrocarbon group or an aliphatic cyclic group; and R' represents an acid dissociable, dissolution inhibiting group.

6 Claims, No Drawings

FOREIGN PATENT DOCUMENTS

WO  WO 2004/074242 A2  9/2004

OTHER PUBLICATIONS

Jin-Baek Kim, Hyo-Jin Yun and Young-Gil Kwon: *Novel Molecular Resist Based on Derivative of Cholic Acid*, Chemistry Letters (2002), pp. 1064-1065.

E. Fukuzaki et al., Polymer journal, 2005, vol. 37, No. 4, p. 284-293.

A. Rajca et al., Journal of Organic Chemistry, 1994, vol. 59, No. 23, p. 7099-7107.

International Search Report in connection with corresponding PCT application No. PCT/JP2007/055661, dated Mar. 20, 2007.

* cited by examiner

COMPOUND, POSITIVE RESIST COMPOSITION AND METHOD FOR FORMING RESIST PATTERN

RELATED APPLICATIONS

This application is the U.S. National Phase filing under 35 U.S.C. §371 of PCT/JP2007/055661, filed March 20, 2007, which designated the United States and was published in a language other than English, which claims priority under 35 U.S.C. §119(a)-(d) to Japanese Patent Application No. 2006-169854, filed June 20, 2006. The contents of these applications are incorporated herein by reference in their entireties.

TECHNICAL FIELD

The present invention relates to a compound that can be used for a resist composition, a positive resist composition that includes the compound, and a method for forming a resist pattern that uses the positive resist composition.

BACKGROUND ART

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultraviolet radiation typified by g-line and i-line radiation has been used, but nowadays, mass production of semiconductor elements using KrF excimer lasers and ArF excimer lasers has commenced. Furthermore, research is also being conducted into lithography techniques that use exposure light sources having a wavelength that is even shorter than these excimer lasers, such as $F_2$ excimer lasers, electron beams, EUV (Extreme Ultra Violet radiation), and X rays.

Furthermore, one example of a known pattern-forming material capable of forming a pattern of minute dimensions is a chemically amplified resist, which includes a base material component having a film-forming capability, and an acid generator component that generates acid upon exposure. Chemically amplified resists include negative resists, which undergo a reduction in alkali solubility upon exposure, and positive resists, which display increased alkali solubility upon exposure.

Conventionally, polymers have been used as the base material components within these types of chemically amplified resists, and examples of these polymers include polyhydroxystyrene (PHS), PHS-based resins in which a portion of the hydroxyl groups of a PHS have been protected with acid dissociable, dissolution inhibiting groups, copolymers derived from (meth)acrylate esters, and resins in which a portion of the carboxyl groups within these (meth)acrylate esters have been protected with acid dissociable, dissolution inhibiting groups.

However, when a pattern is formed using a chemically amplified resist that uses one of these polymers as the base material component, a problem arises in that roughness can develop on the upper surface and side wall surfaces of the pattern. For example, roughness on the side wall surfaces of a resist pattern, so-called line edge roughness (LER), can cause distortions around the holes in hole patterns, and fluctuations in the line width in line and space patterns, and consequently has the potential to adversely affect the formation of very fine semiconductor elements.

This problem becomes more significant as the pattern dimensions are reduced. Accordingly, in lithography processes using an electron beam or EUV or the like, because these processes are targeting the formation of very fine patterns with dimensions of several tens of nm, very low levels of roughness that are superior to current levels of pattern roughness are being demanded.

However, the polymers typically used as base materials have a large molecular size (or root mean squared radius per molecule) of several nm. In the developing step of a pattern formation process, the solubility behavior of the resist with respect to the developing solution typically occurs in single molecule units of the base material component, meaning that as long as polymers are used for the base material component, further reductions in the level of roughness will remain extremely difficult to achieve.

In response to these types of problems, resists that employ a low molecular weight material as the base material component have been proposed as potential materials for achieving ultra low levels of roughness. For example, Non-Patent Documents 1 and 2 propose low molecular weight materials having alkali-soluble groups such as hydroxyl groups or carboxyl groups, wherein some or all of these groups have been protected with acid dissociable, dissolution inhibiting groups.

[Non-Patent Document 1] T. Hirayama, D. Shiono, H. Hada and J. Onodera: J. Photopolym. Sci. Technol., 17 (2004), p. 435

[Non-Patent Document 2] Jim-Baek Kim, Hyo-Jin Yun, Young-Gil Kwon: Chemistry Letters (2002), pp. 1064 to 1065.

DISCLOSURE OF INVENTION

Problems to be Solved by the Invention

These types of low molecular weight materials have small molecular sizes in keeping with their lower molecular weights, and as such, are expected to enable reductions in the level of roughness. Accordingly, there are now growing demands for novel low molecular weight materials that can be used for resist compositions.

The present invention takes the above circumstances into consideration, with an object of providing a compound that can be used for a resist composition, a positive resist composition that includes the compound, and a method for forming a resist pattern that uses the positive resist composition.

Means to Solve the Problems

In order to achieve the above object, a first aspect of the present invention is a compound represented by a general formula (A-1) shown below.

[Chemical Formula 1]

(A-1)

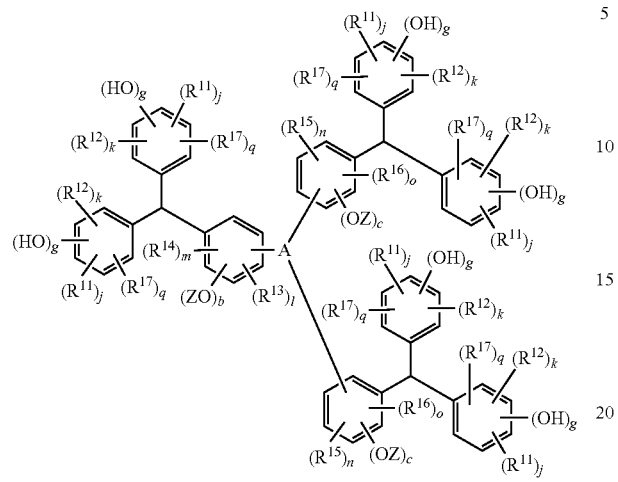

[wherein, $R^{11}$ to $R^{17}$ each independently represents an alkyl group or an aromatic hydrocarbon group of 1 to 10 carbon atoms, which may include a hetero atom within the structure; g and j each independently represents an integer of 1 or greater, and k and q each represents an integer of 0 or greater, provided that g+j+k+q is not greater than 5; b represents an integer of 1 or greater, and l and m each independently represents an integer of 0 or greater, provided that b+l+m is not greater than 4; c represents an integer of 1 or greater, and n and o each independently represents an integer of 0 or greater, provided that c+n+o is not greater than 4; A represents a trivalent aromatic cyclic group, a trivalent alkyl group, a trivalent aliphatic cyclic group, or a trivalent organic group having an aromatic cyclic group or an aliphatic cyclic group; and Z represents a goup represented by general formula (z1) shown below.]

[Chemical Formula 2]

(z1)

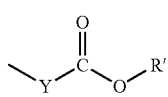

[wherein, Y represents an alkylene group, a divalent aromatic hydrocarbon group, a divalent aliphatic cyclic group, or a divalent organic group having an aromatic hydrocarbon group or an aliphatic cyclic group; and R' represents an acid dissociable, dissolution inhibiting group.]

Furthermore, a second aspect of the present invention is a positive resist composition that includes a base material component (A) that exhibits increased alkali solubility under the action of acid, and an acid generator component (B) that generates acid upon irradiation, wherein the base material component (A) contains a compound (A1) represented by general formula (A-1) shown below.

[Chemcial Formual 3]

(A-1)

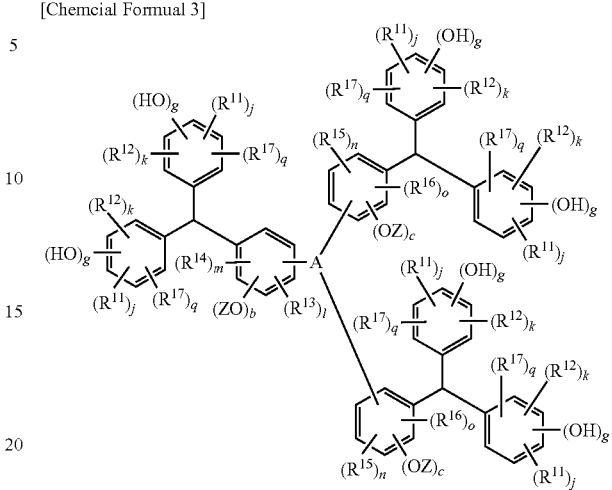

[wherein, $R^{11}$ to $R^{17}$ each independently represents an alkyl group or an aromatic hydrocarbon group of 1 to 10 carbon atoms, which may include a hetero atom within the structure; g and j each independently represents an integer of 1 or greater, and k and q each represents an integer of 0 or greater, provided that g+j+k+q is not greater than 5; b represents an integer of 1 or greater, and l and m each independently represents an integer of 0 or greater, provided that b+l+m is not greater than 4; c represents an integer of 1 or greater, and n and o each independently represents an integer of 0 or greater, provided that c+n+o is not greater than 4; A represents a trivalent aromatic cyclic group, a trivalent alkyl group, a trivalent aliphatic cyclic group, or a trivalent organic group having an aromatic cyclic group or an aliphatic cyclic group; and Z represents a group represented by general formula (z1) shown below.]

[Chemical Formula 4]

(z1)

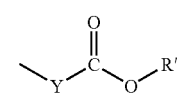

[wherein, Y represents an alkylene group, a divalent aromatic hydrocarbon group, a divalent aliphatic cyclic group, or a divalent organic group having an aromatic hydrocarbon group or an aliphatic cyclic group; and R' represents an acid dissociable, dissolution inhibiting group.]

Furthermore, a third aspect of the present invention is a method for forming a resist pattern that includes: forming a resist film on a substrate using a positive resist composition according to the second aspect described above, exposing the resist film, and developing the resist film to form a resist pattern.

In the present description and claims, an "alkyl group" includes linear, branched and cyclic monovalent saturated hydrocarbon groups, unless otherwise specified.

The term "aliphatic" is a relative concept used in relation to the term "aromatic", and defines a group or compound or the like that has no aromaticity. The term "aliphatic cyclic group" describes a monocyclic group or polycyclic group that has no aromaticity.

An "aromatic cyclic group" describes a cyclic group that has aromaticity. Further, an "aromatic cyclic group" may be either a monocyclic group or polycyclic group that has aromaticity.

Effect of the Invention

According to the present invention, there are provided a novel compound that can be used for a resist composition, a positive resist composition that includes the compound, and a method for forming a resist pattern that uses the positive resist composition.

BEST MODE FOR CARRYING OUT THE INVENTION

<<Compound>>

The compound of the present invention (hereafter frequently referred to as "compound (A1)") is represented by general formula (A-1) shown above.

In general formula (A-1), Z is a group represented by general formula (z1) shown above. Y represents an alkylene group, a divalent aromatic hydrocarbon group, a divalent aliphatic cyclic group, or a divalent organic group having an aromatic hydrocarbon group or an aliphatic cyclic group.

When Y represents an alkylene group, an alkylene group of 1 to 5 carbon atoms is preferred, an alkylene group of 1 to 3 carbon atoms is more preferred, a methylene group, ethylene group or propylene group is still more preferred, and a methylene group is the most desirable.

When Y represents a divalent aromatic hydrocarbon group, aromatic hydrocarbon groups of 6 to 16 carbon atoms may be exemplified. Specific examples include groups in which two hydrogen atoms have been removed from benzene, naphthalene, anthracene, phenanthrene or pyrene.

When Y represents a divalent aliphatic cyclic group, groups in which two hydrogen atoms have been removed from the basic ring structure (namely, the basic ring exclusive of substituents) of the cyclic alkyl group for $R^1$ described below may be exemplified.

When Y represents a divalent organic group having an aromatic hydrocarbon group or an aliphatic cyclic group, the aromatic hydrocarbon group or aliphatic cyclic group are as described above, whereas examples of the organic group include alkylene groups of 1 to 5 carbon atoms.

The acid dissociable, dissolution inhibiting group (R') is a group that has an alkali dissolution inhibiting effect that renders the compound (A1) insoluble in alkali prior to dissociation, but then upon dissociation, causes the compound (A1) to change to an alkali-soluble state. Accordingly, when the compound (A1) is blended into a positive resist composition together with the acid generator component (B) in the manner described below, the action of the acid generated from the acid generator component (B) by exposure causes the acid dissociable, dissolution inhibiting groups to dissociate, thereby making the compound (A1) change from an alkali-insoluble state to an alkali-soluble state. In this description, the general concept of an "acid dissociable, dissolution inhibiting group" includes groups containing an acid dissociable, dissolution inhibiting group.

There are no particular limitations on the acid dissociable, dissolution inhibiting group, which may be selected appropriately from those groups proposed for use within chemically amplified resist compositions designed for use with KrF or ArF excimer lasers. Specific examples include tertiary alkyl groups, tertiary alkyloxycarbonyl groups, alkoxycarbonylalkyl groups, alkoxyalkyl groups, and cyclic ether groups.

Specific examples of the tertiary alkyl groups include chain-like tertiary alkyl groups such as a tert-butyl group, tert-amyl group, tert-pentyl group or tert-heptyl group, and tertiary alkyl groups that contain an aliphatic monocyclic or polycyclic cyclic group, such as a 2-methyl-2-adamantyl group, 2-ethyl-2-adamantyl group, 1-ethyl-1-cyclohexyl group, 1-methyl-1-cyclohexyl group, 1-ethyl-1-cyclopentyl group or 1-methyl-1-cyclopentyl group. The number of carbon atoms within these tertiary alkyl groups is preferably from 4 to 20.

The aliphatic cyclic group may be either saturated or unsaturated, but is preferably saturated.

Examples of the tertiary alkyl group within a tertiary alkyloxycarbonyl group include the same tertiary alkyl groups as those listed above. Specific examples of the tertiary alkyloxycarbonyl groups include a tert-butyloxycarbonyl group and a tert-amyloxycarbonyl group.

Specific examples of the cyclic ether groups include a tetrahydropyranyl group and a tetrahydrofuranyl group. The number of carbon atoms within these cyclic ether groups is preferably from 5 to 10.

In the present invention, compounds that include, as the group R', at least one acid dissociable, dissolution inhibiting group selected from the group consisting of alkoxycarbonylalkyl groups represented by general formula (p1) shown below, and alkoxyalkyl groups represented by general formula (p2) shown below are preferred as such compounds yield superior effects for the present invention.

[Chemical Formula 5]

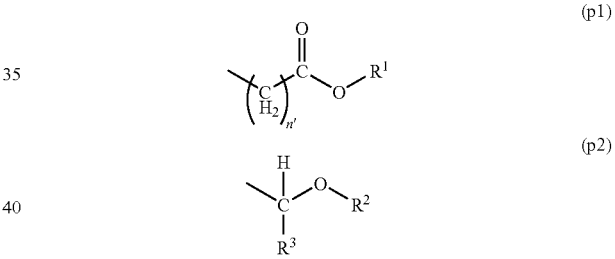

[wherein, $R^1$ and $R^2$ each independently represents a linear, branched or cyclic alkyl group, which may include a hetero atom within the structure; $R^3$ represents a hydrogen atom or a lower alkyl group; and n' represents an integer of 1 to 3.]

In general formula (p1), n' represents an integer of 1 to 3, and is preferably 1.

$R^1$ represents a linear, branched or cyclic alkyl group, which may include a hetero atom within the structure. In other words, in the alkyl group represented by $R^1$, some or all of the hydrogen atoms may be substituted with a group that contains a hetero atom (including those cases where the hetero atom itself functions as the substituent), or a portion of the carbon atoms of the alkyl group may be substituted with a hetero atom.

Examples of the hetero atom include an oxygen atom, sulfur atom, nitrogen atom, and fluorine atom.

A "group that contains a hetero atom" may be the hetero atom itself, or a group composed of the hetero atom and one or more carbon atoms and/or hydrogen atoms, such as an alkoxy group.

Examples of alkyl groups in which some or all of the hydrogen atoms have been substituted with a hetero atom include fluorinated lower alkyl groups of 1 to 5 carbon atoms in which some or all of the hydrogen atoms have been substituted with fluorine atoms, groups in which two hydrogen atoms bonded to the same carbon atom have been substituted with a single oxygen atom (namely, groups containing a carbonyl group (C=O)), and groups in which two hydrogen atoms bonded to the same carbon atom have been substituted with a single sulfur atom (namely, groups containing a thiocarbonyl group (C=S)).

Examples of groups in which a portion of the carbon atoms of an alkyl group have been substituted with a group that contains a hetero atom include examples in which a carbon atom has been substituted with a nitrogen atom (for example, branched or cyclic alkyl groups containing a —$CH_2$— group within the structure, wherein the —$CH_2$— has been substituted with a —NH— group), and examples in which a carbon atom has been substituted with an oxygen atom (for example, branched or cyclic alkyl groups containing a —$CH_2$— group within the structure, wherein the —$CH_2$— has been substituted with a —O— group).

The linear alkyl group for R' preferably contains from 1 to 5 carbon atoms, and specific examples include a methyl group, ethyl group, n-propyl group, n-butyl group, isobutyl group or n-pentyl group, and a methyl group or ethyl group is particularly preferred.

The branched alkyl group for $R^1$ preferably contains from 4 to 10 carbon atoms, and even more preferably 4 to 8 carbon atoms. Specific examples include an isobutyl group, tert-butyl group, isopentyl group, neopentyl group or tert-pentyl group, and a tert-butyl group is particularly preferred.

The cyclic alkyl group for $R^1$ preferably contains from 3 to 20 carbon atoms, more preferably from 4 to 14 carbon atoms, and most preferably from 5 to 12 carbon atoms.

The basic ring structure within the cyclic alkyl group (the basic ring exclusive of substituents) may be either monocyclic or polycyclic, although a polycyclic structure yields particularly superior effects for the present invention and is consequently preferred. Furthermore, the basic ring may be either a hydrocarbon ring formed solely from carbon and hydrogen, or a heterocycle in which a portion of the carbon atoms that constitute a hydrocarbon ring have been substituted with hetero atoms. In the present invention, groups in which the basic ring structure is a hydrocarbon ring are preferred. Examples of the hydrocarbon ring include monocycloalkanes, bicycloalkanes, tricycloalkanes and tetracycloalkanes. Specific examples include monocycloalkanes such as cyclopentane and cyclohexane, and polycycloalkanes such as adamantane, norbornane, isobornane, tricyclodecane, and tetracyclododecane. Of these, adamantane, norbornane, tricyclodecane and tetracyclododecane are preferred, and adamantane is particularly desirable.

These basic ring structures may include a substituent on the ring, or may have no substituents.

Examples of the substituent include lower alkyl groups, a fluorine atom, fluorinated lower alkyl groups, and an oxygen atom (=O). Examples of the lower alkyl groups include linear or branched alkyl groups of 1 to 5 carbon atoms such as a methyl group or ethyl group. In those cases where the basic ring structure includes a substituent, the number of substituents is preferably within a range from 1 to 3, and is most preferably 1. The expression "includes a substituent" means that a hydrogen atom bonded to a carbon atom that constitutes part of the basic ring structure has been substituted with the substituent.

A cyclic alkyl group for $R^1$ is a group in which one hydrogen atom has been removed from the above type of basic ring structure. In $R^1$, the carbon atom bonded to the oxygen atom adjacent to $R^1$ is preferably one of the carbon atoms that constitute the above type of basic ring structure, and groups in which the carbon atom bonded to the oxygen atom adjacent to the $R^1$ group is a tertiary carbon atom to which a substituent such as a lower alkyl group is also bonded yield particularly superior effects for the present invention and are consequently preferred.

Examples of acid dissociable, dissolution inhibiting groups having a cyclic alkyl group as $R^1$ include groups represented by formulas (p1-1) to (p1-7) shown below. Of these, groups represented by general formula (p1-1) are preferred.

[Chemical Formula 6]

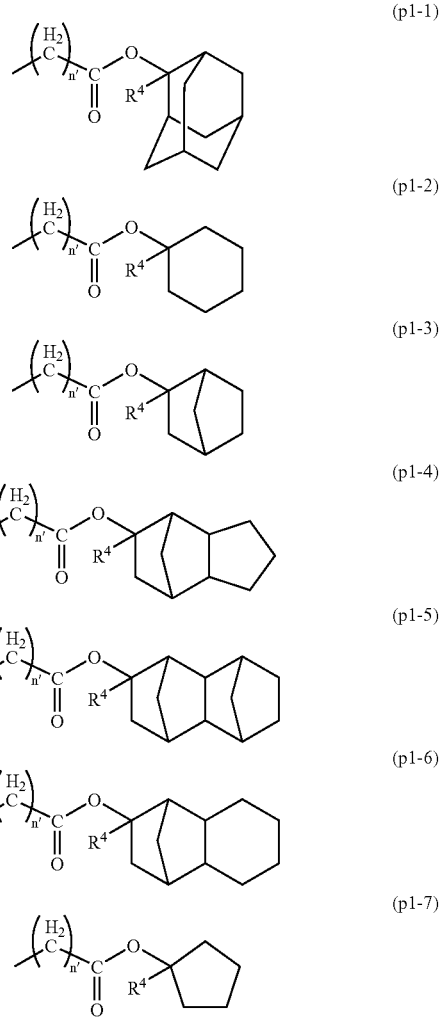

[wherein, $R^4$ represents a lower alkyl group, and n' is as defined above.]

The lower alkyl group for $R^4$ is an alkyl group of 1 to 5 carbon atoms, and specific examples include linear or branched lower alkyl groups such as a methyl group, ethyl group, propyl group, isopropyl group, n-butyl group, isobutyl group, tert-butyl group, pentyl group, isopentyl group, and neopentyl group. In terms of industrial availability, $R^4$ is preferably a methyl group or an ethyl group, and a methyl group is particularly desirable.

$R^1$ is preferably an acid dissociable, dissolution inhibiting group having a cyclic alkyl group.

In formula (p2), examples of R² include the same groups as those exemplified above for R¹. Of these, R² is preferably a linear alkyl group or a cyclic alkyl group.

R³ represents a hydrogen atom or a lower alkyl group. The lower alkyl group for R³ is an alkyl group of 1 to 5 carbon atoms, and specific examples include linear or branched lower alkyl groups such as a methyl group, ethyl group, propyl group, isopropyl group, n-butyl group, isobutyl group, tert-butyl group, pentyl group, isopentyl group and neopentyl group. In terms of industrial availability, R³ is preferably a hydrogen atom or a methyl group, and a hydrogen atom is particularly desirable.

Examples of groups represented by formula (p2) when R² is a linear alkyl group include a 1-ethoxyethyl group, 1-ethoxymethyl group, 1-methoxyethyl group, 1-methoxymethyl group, 1-methoxypropyl group, 1-ethoxypropyl group, 1-n-butoxyethyl group, 1-pentafluoroethoxyethyl group, 1-trifluoromethoxyethyl group, and 1-trifluoromethoxymethyl group.

Examples of groups represented by formula (p2) when R² is a cyclic alkyl group include groups represented by the formulas shown below.

[Chemical Formula 7]

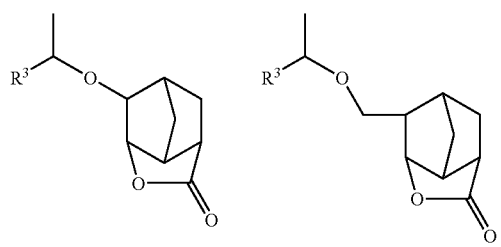

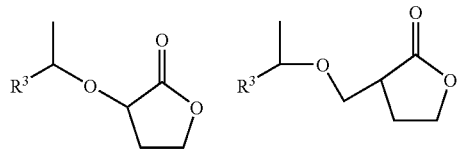

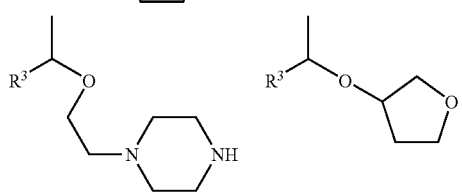

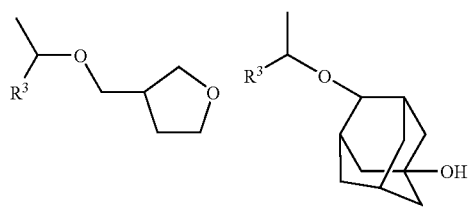

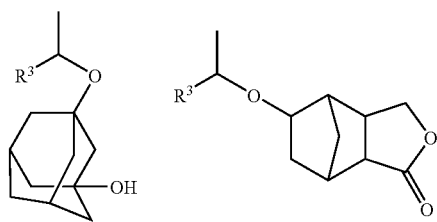

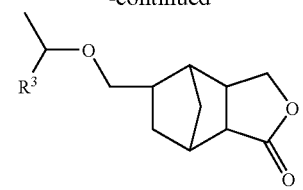

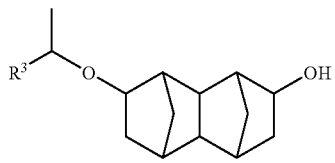

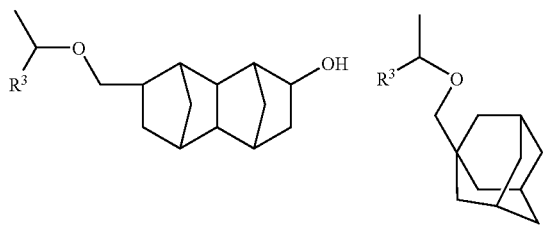

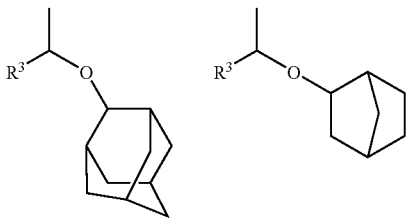

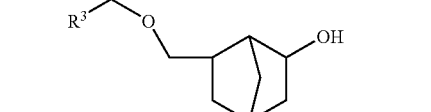

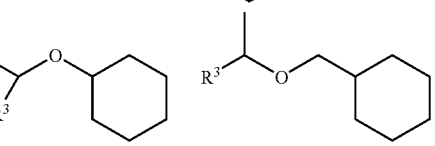

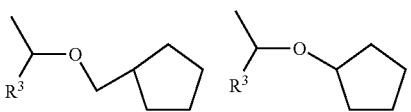

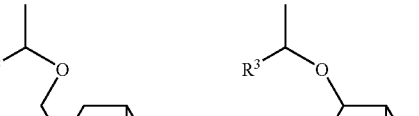

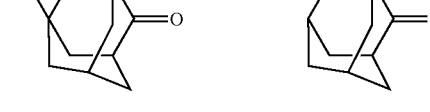

[wherein, R³ is as defined above.]

Of these, groups represented by general formulas (p2-1) and (p2-2) shown below are particularly preferred.

[Chemical Formula 8]

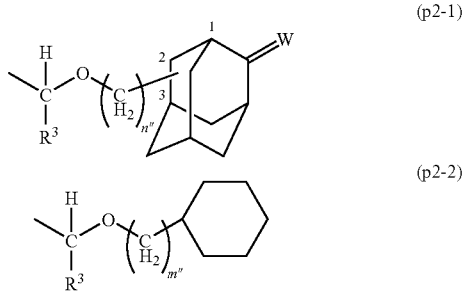

[wherein, $R^3$ is as defined above, n" and m" each independently represents an integer of 0 to 2, and W represents either two hydrogen atoms or an oxygen atom.]

n" and m" are most preferably either 0 or 1.

There are no particular limitations on the bonding position between the adamantyl group and the —$CHR^3$—O—$(CH_2)_{n''}$— group, although bonding at either position 1 or position 2 of the adamantyl group is preferred.

In the present invention, the acid dissociable, dissolution inhibiting group is preferably a group having a cyclic group, such as the groups represented by the above formulas (p1-1) to (p1-7) and (p2-1) to (p2-2), as such groups yield superior effects for the present invention. Compared with those cases where the acid dissociable, dissolution inhibiting group is a chain-like group, acid dissociable, dissolution inhibiting groups having a cyclic group result in a lower alkali solubility for the compound (A1). As a result, when the compound (A1) is blended into a positive resist composition, the resistance to alkali developing solutions is increased for the unexposed portions of a resist film formed using the positive resist composition.

In other words, the difference in alkali solubility between the exposed portions and the unexposed portions (the solubility contrast) increases, and the resolution improves.

In the present invention, the properties of the compound (A1) such as the alkali solubility can be adjusted by appropriate selection of the acid dissociable, dissolution inhibiting group. In other words, in the compound (A1), when the acid dissociable, dissolution inhibiting group is introduced, because the reactivity of the carboxyl groups is higher than that of the hydroxyl groups, the acid dissociable, dissolution inhibiting group is introduced at the carboxyl group within the Z groups. As a result, besides the Z groups, the remaining portions of the compound structure remain unchanged, meaning that compared with the polymers and the like used as the base material components of conventional positive resist compositions, structural variation between molecules is extremely small. Accordingly, the properties of the entire compound (A1) can be adjusted by appropriate selection of the acid dissociable, dissolution inhibiting group. For example, if a comparison is made between a case where a group having a polycyclic structure such as an adamantane ring is selected as the acid dissociable, dissolution inhibiting group, a case where a group having a monocyclic structure such as a cyclohexane ring is selected, and a case where a group having a chain-like structure is selected, then the alkali solubility of the compound (A1) satisfies the expression: group having a polycyclic structure<group having a monocyclic structure<group having a chain-like structure.

Due consideration is preferably given to the structures of $R^{11}$ to $R^{17}$ when selecting the acid dissociable, dissolution inhibiting group. This enables the alkali solubility of the compound (A1) to be adjusted to a value within an ideal range for use within a positive resist composition. For example, in those cases where $R^{11}$ to $R^{17}$ are chain-like alkyl groups such as methyl groups, the alkali solubility of the compound (A1) tends to be high, but by selecting a group having a polycyclic structure such as an adamantane ring as the acid dissociable, dissolution inhibiting group, the alkali solubility of the compound (A1) can be reduced. Furthermore, in those cases where $R^{11}$ to $R^{17}$ are cyclic alkyl groups such as cyclohexyl groups or aromatic hydrocarbon groups, the alkali solubility of the compound (A1) tends to be low, but in these cases, by combining these groups with a group having a monocyclic structure such as a cyclohexane ring as the acid dissociable, dissolution inhibiting group, the alkali solubility of the compound (A1) can be increased.

$R^{11}$ to $R^{17}$ each independently represents a linear, branched or cyclic alkyl group or an aromatic hydrocarbon group of 1 to 10 carbon atoms.

The alkyl group is preferably a linear or branched lower alkyl group of 1 to 5 carbon atoms, or a cyclic alkyl group of 5 to 6 carbon atoms. Examples of the lower alkyl group include linear or branched alkyl groups such as a methyl group, ethyl group, propyl group, isopropyl group, n-butyl group, isobutyl group, tert-butyl group, pentyl group, isopentyl group and neopentyl group, and of these, a methyl group is preferred. Examples of the cyclic alkyl group include a cyclohexyl group and cyclopentyl group, and a cyclohexyl group is preferred.

Examples of the aromatic hydrocarbon group include a phenyl group, tolyl group, xylyl group, mesityl group, phenethyl group and naphthyl group.

These alkyl groups or aromatic hydrocarbon groups may include a hetero atom such as an oxygen atom, nitrogen atom or sulfur atom within the group structure.

g and j each independently represents an integer of 1 or greater, and k and q each independently represents an integer of 0 or greater, provided that g+j+k+q is not greater than 5.

g and j are preferably either 1 or 2, and are most preferably 1.

k is preferably an integer of 0 to 2, more preferably either 0 or 1, and most preferably 1.

q is preferably an integer of 0 to 2, more preferably either 0 or 1, and most preferably 0.

b is an integer of 1 or greater, and l and m each independently represents an integer of 0 or greater, provided that b+l+m is not greater than 4.

b is preferably either 1 or 2, and is most preferably 1.

l is preferably an integer of 0 to 2, more preferably either 0 or 1, and most preferably 1.

m is preferably an integer of 0 to 2, more preferably either 0 or 1, and most preferably 0.1+m is most preferably 1.

c is an integer of 1 or greater, and n and o each independently represents an integer of 0 or greater, provided that c+n+o is not greater than 4.

c is preferably either 1 or 2, and is most preferably 1.

n is preferably an integer of 0 to 2, more preferably either 0 or 1, and most preferably 1.

o is preferably an integer of 0 to 2, more preferably either 0 or 1, and most preferably 0. n+o is most preferably 1.

There are no particular limitations on the bonding position of the groups [—OZ] bearing the subscript b or c, but these —OZ groups are preferably bonded at least to the para position relative to the group A that is bonded to the benzene ring to which the —OZ group is bonded. These compounds offer certain advantages, including the fact that a low molecular weight compound produced using such a compound is ideal for use within a resist composition, and the fact that the compounds are readily synthesized.

There are no particular limitations on the bonding position of the hydroxyl groups bearing the subscript g, although in terms of using the resulting compound to produce a low molecular weight compound that is ideal for use within resist compositions, and ensuring ready synthesis, compounds in which these hydroxyl groups are bonded to at least the para position (position 4) of the phenyl groups are preferred.

There are no particular limitations on the bonding positions of the groups $R^{11}$, $R^{12}$ and $R^{17}$, but in terms of factors such as the ease of synthesis, $R^{11}$ is preferably bonded to at least one of the carbon atoms adjacent to a carbon atom bearing a hydroxyl group.

In the present invention, A represents a trivalent aromatic cyclic group, a trivalent alkyl group, a trivalent aliphatic cyclic group, or a trivalent organic group having an aromatic cyclic group or an aliphatic cyclic group.

The trivalent aromatic cyclic group, trivalent alkyl group, trivalent aliphatic cyclic group, or trivalent organic group having an aromatic cyclic group or an aliphatic cyclic group represented by A may or may not include a substituent. Examples of the substituent include a lower alkyl group of 1 to 5 carbon atoms, a fluorine atom, a fluorinated lower alkyl group of 1 to 5 carbon atoms substituted with a fluorine atom, and an oxygen atom (=O).

Examples of the trivalent aromatic cyclic group for A include groups in which three hydrogen atoms have been removed from an aromatic compound such as benzene, naphthalene, anthracene, phenanthrene or pyrene.

Examples of the trivalent alkyl group for A include groups in which three hydrogen atoms have been removed from an alkane of 1 to 5 carbon atoms. The group may be either linear or branched.

As the trivalent aliphatic cyclic group for A, although the basic ring structure exclusive of substituents is not limited to a group formed solely from carbon and hydrogen (a hydrocarbon group), a hydrocarbon group is preferred. Further, the "hydrocarbon group" may be either saturated or unsaturated, but is typically saturated. A polycyclic group is particularly preferred.

Specific examples of this type of trivalent aliphatic cyclic group include groups in which three hydrogen atoms have been removed from a monocycloalkane; and groups in which three hydrogen atoms have been removed from a polycycloalkane such as a bicycloalkane, tricycloalkane or tetracycloalkane. Specific examples include groups in which three hydrogen atoms have been removed from a monocycloalkane such as cyclopentane or cyclohexane, and groups in which three hydrogen atoms have been removed from a polycycloalkane such as adamantane, norbornane, isobornane, tricyclodecane and tetracyclododecane. In these groups, some or all of the hydrogen atoms may be substituted with substituents (such as a lower alkyl group, a fluorine atom or a fluorinated alkyl group).

Of these possibilities, an aliphatic cyclic group of 4 to 15 carbon atoms is preferred, a group in which three hydrogen atoms have been removed from adamantane is more preferred, and groups in which the hydrogen atoms have been removed from position 1 and position 3 of adamantane are particularly desirable.

Moreover, a trivalent organic group having an aromatic cyclic group or an aliphatic cyclic group may also be used as A.

Examples of the trivalent organic group having an aromatic cyclic group represented by A include groups formed from organic compounds having 1 to 3 lower alkyl groups of 1 to 5 carbon atoms added to an aromatic compound such as benzene, naphthalene, anthracene, phenanthrene or pyrene, wherein three hydrogen atoms have been removed from these lower alkyl groups.

Examples of the trivalent organic group having an aliphatic cyclic group represented by A include groups formed from organic compounds having 1 to 3 lower alkyl groups of 1 to 5 carbon atoms added to a monocycloalkane, wherein three hydrogen atoms have been removed from these lower alkyl groups, and groups formed from organic compounds having 1 to 3 lower alkyl groups of 1 to 5 carbon atoms added to a polycycloalkane such as a bicycloalkane, tricycloalkane or tetracycloalkane, wherein three hydrogen atoms have been removed from these lower alkyl groups.

As the group A, a trivalent alkyl group or a trivalent organic group having an aromatic cyclic group is preferred, and a trivalent organic group having an aromatic cyclic group is particularly desirable.

As the compound (A1) of the present invention compounds represented by general formula (A-1-1) and compounds represented by general formula (A-2) shown below are preferred, as compounds produced using such compounds are ideal for use within resist compositions.

[Chemical Formula 9]

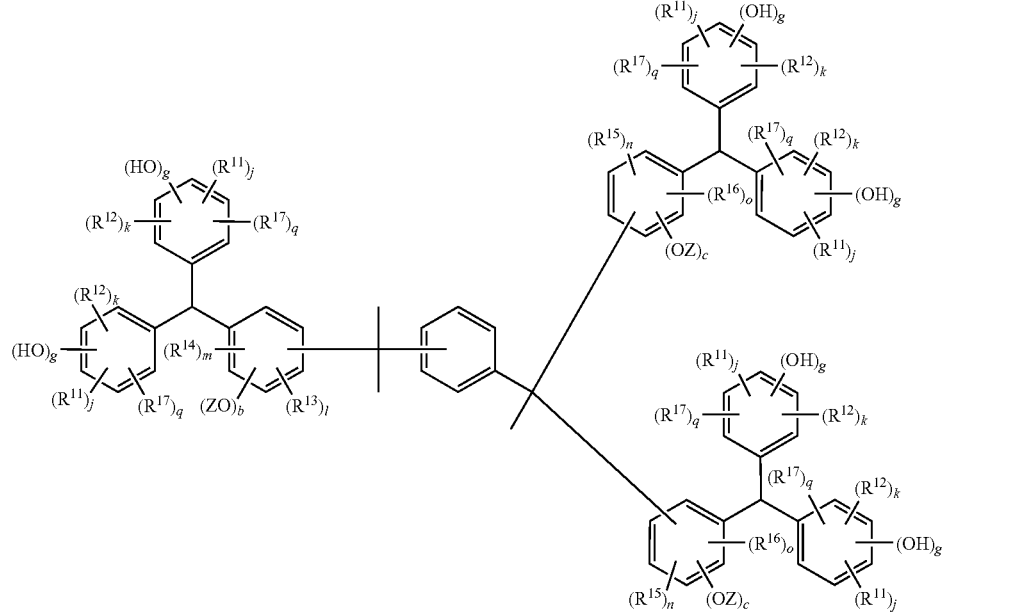

(A-1-1)

[wherein, $R^{11}$ to $R^{17}$, g, j, k, q, g+j+k+q, b, l, m, b+l+m, c, n, o, c+n+o, and Z are as defined above for formula (A-1).]

[Chemical Formula 10]

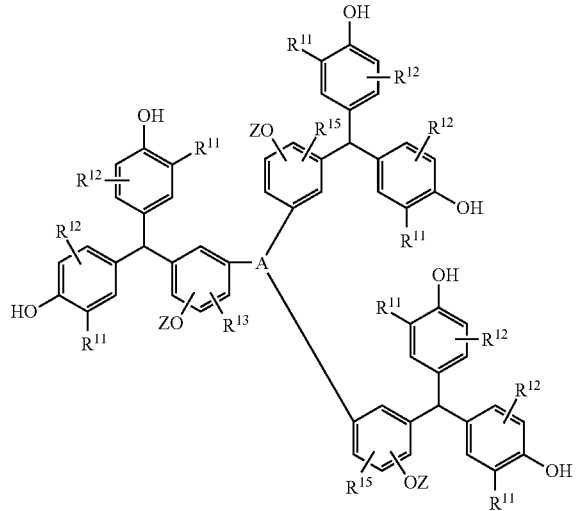

(A-2)

[wherein, $R^1$, $R^{12}$, $R^{13}$, $R^{15}$, A and Z are as defined above for formula (A-1).]

Of the compounds represented by formula (A-2), compounds represented by general formula (A-2-1) shown below are preferred.

[Chemical Formula 11]

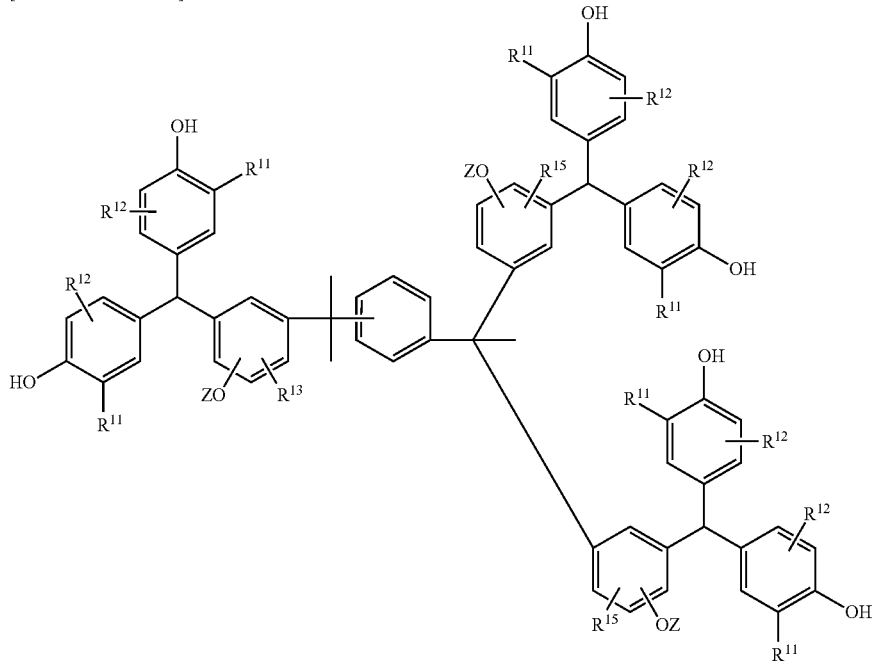

(A-2-1)

[wherein, $R^{11}$, $R^{12}$, $R^{13}$, $R^{15}$, and Z are as defined above for formula (A-2).]

$R^{12}$ is preferably bonded to the 2nd or 3rd position of the phenyl group. OZ is preferably bonded to the 4th position of the phenyl group. $R^{13}$ and $R^{15}$ are preferably bonded to the 3rd position of their respective phenyl groups.

The compound (A1) is a material that is capable of forming an amorphous (non-crystalline) film using a spin coating method. Here, an "amorphous film" refers to an optically transparent film that does not crystallize. Spin coating is one of the most commonly used methods for forming thin films.

A judgment as to whether or not the compound is capable of forming an amorphous film using spin coating is determined on the basis of whether or not a coating film formed by spin coating the compound onto an 8-inch silicon wafer is transparent across the entire film surface. More specifically, judgment can be conducted, for example, in the manner described below. First, the compound is added to a solvent typically used as a resist solvent, such as a mixed solvent of ethyl lactate and propylene glycol monoethyl ether acetate in a ratio (weight ratio) of 40/60 (hereafter this solvent is abbreviated as EM), in sufficient quantity to generate a solution with a concentration of 14% by weight, and dissolution of the compound is achieved by ultrasound treatment (dissolution treatment) using an ultrasonic cleaning apparatus. The resulting solution is spin coated onto a wafer at 1,500 rpm and subjected to optional drying and baking (PAB, Post Applied Bake) at 110° C. for 90 seconds, and a visual judgment is then made as to whether the formed coating film is transparent, thereby confirming whether or not an amorphous film has been formed. A non-transparent, cloudy film is not an amorphous film.

In the present invention, the compound (A1) preferably generates an amorphous film via the above method that exhibits favorable stability, and for example, compounds for which the amorphous state of the coating film is retained even after standing for two weeks at room temperature following the above PAB treatment are particularly desirable.

The compound (A1) can be produced by using known methods to substitute the hydrogen atoms at the terminals of the carboxyl groups within groups Z' in a compound (J1)

represented by general formula (J) shown below with acid dissociable, dissolution inhibiting groups.

[Chemical Formula 12]

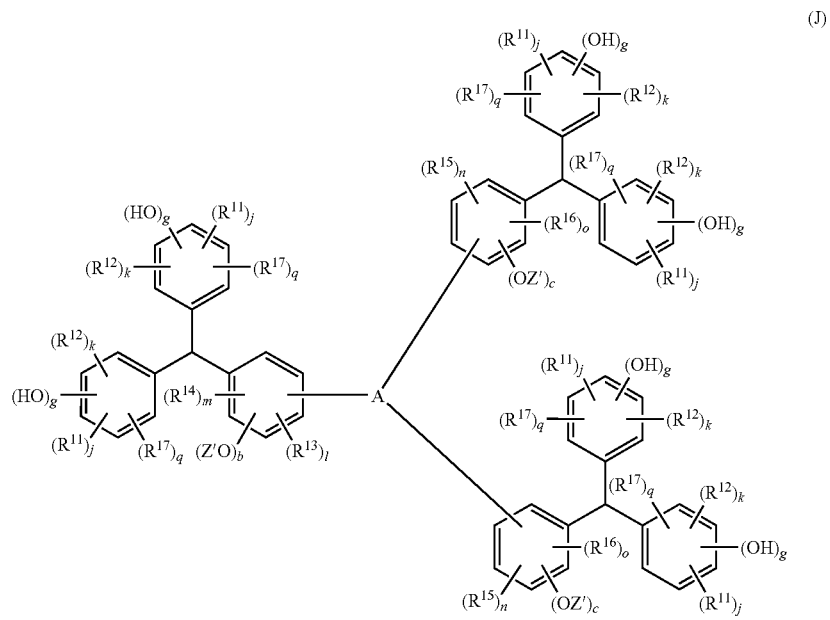
(J)

[wherein, $R^{11}$ to $R^{17}$, g, j, k, q, b, l, m, c, n, o and A are as defined above for $R^{11}$ to $R^{17}$, g, j, k, q, b, l, m, c, n, o and A respectively within general formula (A-1), and Z' is represented by general formula (Jz) shown below.]

[Chemical Formula 13]

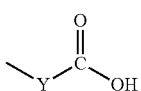
(Jz)

[wherein, Y is as defined above for Y in formula (z1).]

The compound (J1) can be produced by conventional methods, for example by subjecting a trisalicylaldehyde derivative, in which three salicylaldehydes (which may have substituents) are bonded together via the group A, and a phenol compound having a substituent group to a dehydration-condensation under acidic conditions, thereby generating a tris(triphenylmethane) derivative, and then introducing —Y—COOH groups by reacting a halogenated carboxylic acid such as Br—Y—COOH with the hydroxyl groups of the tris(triphenylmethane) derivative. However, in this type of conventional method, controlling the hydroxyl group positions and the number of hydroxyl groups at which the —Y—COOH groups are introduced is difficult, and the yield tends to be low for the compound (J1) in which —Y—COOH groups are bonded to the three benzene rings linked via the group A.

As a result, the compound (J1) is preferably produced using a production method that includes:
reacting a compound (J-1) represented by general formula (J-1) shown below with a compound (J-2) represented by general formula (J-2) shown below to obtain a compound (J-3) represented by general formula (J-3) shown below (hereafter referred to as the "compound (J-3) formation step"), and producing the compound (J1) (hereafter referred to as the "compound (J1) formation step") via a step of reacting the compound (J-3) with a compound (J-4) represented by general formula (J-4) shown below under acidic conditions.

[Chemical Formula 14]

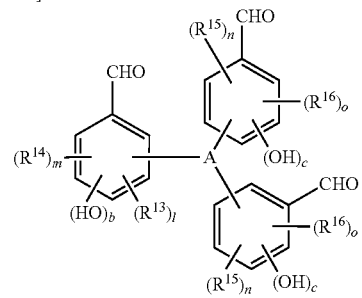
(J-1)

[Chemical Formula 15]

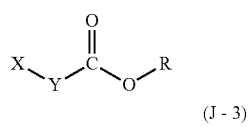
(J-2)

[Chemical Formula 16]

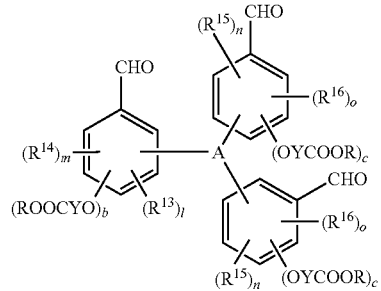
(J-3)

-continued (J-4)

[Chemical Formula 17]

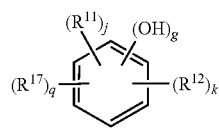

In formulas (J-1) to (J-4), X represents a halogen atom, R represents a protective group, and $R^{11}$ to $R^{17}$, g, j, k, q, b, l, m, c, n, o and A are as defined above for $R^{11}$ to $R^{17}$, g, j, k, q, b, l, m, c, n, o and A respectively within formulas (A-1) and (J). Y is as defined above.

<Compound (J-3) Formation Step>

In general formula (J-2), examples of the halogen atom represented by X include a bromine atom, chlorine atom or fluorine atom. A bromine atom or chlorine atom is preferred as these atoms offer superior reactivity.

There are no particular limitations on the protective group represented by R, provided it does not react during the reaction between the compound (J-1) and the compound (J-2), and is either an acid dissociable group that dissociates under the acidic conditions used during reaction of the compound (J-3) in the subsequent compound (J1) formation step, or a group that dissociates via hydrolysis. This group may be selected appropriately from the many groups that have been proposed as protective groups.

Examples of the protective group include the same groups as those exemplified above as the acid dissociable, dissolution inhibiting group within the group Z in formula (A-1).

The compound (J-1) and the compound (J-2) can be reacted using conventional methods, for example by dissolving the compound (J-1) in an organic solvent such as acetone, adding a base such as potassium carbonate to the solution, and then adding the compound (J-2) to the stirred solution of the compound (J-1), in a quantity that provides approximately 2 molar equivalents of the compound (J-2) relative to the compound (J-1).

The organic solvent used during this reaction may be any solvent capable of dissolving the compound (J-1), the compound (J-2) and the produced compound (J-3), and may be selected appropriately from among typical organic solvents. Specific examples of these typical organic solvents include ketones such as acetone, methyl ethyl ketone, methyl amyl ketone and cyclohexanone; ethers such as THF, dioxane, glyme and propylene glycol monomethyl ether; esters such as ethyl acetate and ethyl lactate; ether esters such as propylene glycol methyl ether acetate; and lactones such as γ-butyrolactone. These solvents may be used either alone or as mixtures.

The reaction temperature is preferably within a range from 10 to 80° C., more preferably from 40 to 80° C., and most preferably from 60 to 80° C.

The reaction time is preferably within a range from 1 to 24 hours, and more preferably from 4 to 15 hours.

Following completion of the reaction, the reaction solution may be used, without modification, in the following step, or water/ethyl acetate or the like may be added, and the organic phase (the phase within the ethyl acetate or the like) then concentrated under reduced pressure to obtain the compound (J-3).

<Compound (J1) Formation Step>

In this step, first, a step is conducted in which the compound (J-3) and the compound (J-4) are reacted under acidic conditions. This step results in a reaction between the formyl groups (—CHO) of the compound (J-3) and the compound (J-4), as well as the dissociation of the protective groups R from the compound (J-3), thereby forming carboxyl groups.

Specifically, the reaction can be conducted, for example, by dissolving approximately 4 molar equivalents of the compound (J-4) relative to the compound (J-3) within an organic solvent such as methanol, adding an acid such as hydrochloric acid to the solution, and then adding the compound (J-3).

There are no particular limitations on the acid used during this step, provided the compound (J-3) and the compound (J-4) undergo reaction and the protective groups R dissociate. Specific examples of preferred acids include hydrochloric acid, sulfuric acid, sulfuric anhydride, p-toluenesulfonic acid, methanesulfonic acid, trifluoromethanesulforic acid, oxalic acid, formic acid, phosphoric acid, trichloroacetic acid and trifluoroacetic acid. Hydrochloric acid is particularly favorable. These acids may be used either alone, or in mixtures of two or more different acids.

The amount of acid added, for example in the case of a 35 wt % hydrochloric acid, is typically within a range from 1 to 700 parts by weight, and preferably from 10 to 100 parts by weight, relative to 100 parts by weight of the compound (J-3).

The reaction temperature is preferably within a range from 20 to 80° C., and more preferably from 30 to 65° C.

The reaction time is preferably within a range from 2 to 96 hours, and more preferably from 5 to 72 hours.

Following completion of the reaction, a base such as sodium hydroxide is added to the reaction solution to neutralize the acid within the reaction solution. At this time, in those cases where an alcohol such as methanol has been used as the organic solvent for the reaction solution, the produced carboxyl groups may have undergone slight esterification by the alcohol. As a result, in order to hydrolyze such esters, the addition of an excess of base is preferred.

In the thus obtained reaction solution, the compound (J1) is dissolved in the form of a salt. Accordingly, if the reaction solution is transferred to a separating funnel, washed with water/methyl isobutyl ketone or water/diethyl ether or the like to remove any raw materials (such as the compounds used in the reaction), and the water phase is then extracted and neutralized with an aqueous solution of hydrochloric acid, a precipitate develops. The compound (J1) can be obtained by recovering this precipitate by filtration or the like.

This unpurified compound (J1) may be subjected to a purification treatment such as re-precipitation.

As described below, the above compound (A1) can be used favorably as a base material component (A) within a positive resist composition that includes the base material component (A), which exhibits increased alkali solubility under the action of acid, and an acid generator component (B) that generates acid upon irradiation.

By using a positive resist composition containing the compound (A1), a high resolution resist pattern such as an ultra fine resist pattern with pattern dimensions of 200 nm or less can be formed, and the roughness can also be reduced.

It is thought that this effect is due to the uniformity of the compound (A1). In other words, in conventional resists that use a high molecular weight polymer (resin) as the base material component of the resist material, controlling the molecular weight dispersion and the alkali solubility dispersion is very difficult. As a result, there is a limit to the degree of reduction that can be achieved in the LER, which is caused by factors such as these dispersions, and the molecular size itself.

Furthermore, in the case of conventional low molecular weight compounds that have been considered for countering the above problems, because the alkali-soluble groups are protected with acid dissociable, dissolution inhibiting groups as described in the above Non-Patent Documents 1 and 2, variations occur between individual molecules in terms of the positions of the protected alkali-soluble groups and the protection ratio, and as a result, variations also develop in the properties of the compound, causing similar problems to those outlined above.

In contrast, the compound (A1) is a low molecular weight non-polymer. Furthermore, as described above, the compound (J1) used in producing the compound (A1) contains phenolic hydroxyl groups and carboxyl groups as the alkali-soluble groups, meaning that when the alkali-soluble groups are protected with acid dissociable, dissolution inhibiting groups, the more reactive carboxyl groups undergo selective protection. As a result, the resulting compound (A1) exhibits less variation in structure and molecular weight than a compound containing an equivalent quantity of solely hydroxyl groups as the alkali-soluble groups. As a result, the compound (A1) exhibits minimal variation between molecules in terms of properties such as the alkali solubility, the hydrophilicity, and the hydrophobicity, meaning a resist film with more uniform properties can be formed. Accordingly, it is surmised that by using the compound (A1), a resist film with uniform properties can be formed, and that as a result, a high resolution resist pattern can be formed, and the level of roughness can also be reduced.

Moreover, as described above, because the compound (A1) has uniform properties and is thought to enable the formation of a resist film having uniform properties (such as alkali solubility, hydrophilicity and hydrophobicity), use of the compound (A1) also enables a reduction in the level of defects. Here, the term "defects" refers to general abnormalities detected by inspection of the developed resist pattern from directly above the resist pattern, using a surface defect detection device (trade name: "KLA") manufactured by KLA-TENCOR Corporation. Examples of these abnormalities include post-developing scum, foam, dust, bridges across different portions of the resist pattern, color irregularities, and foreign deposits.

Furthermore, because the compound (A1) has uniform properties and is thought to display uniform solubility in organic solvents and the like, the storage stability of a positive resist composition containing the compound (A1) also improves.

Because the compound (A1) includes three triphenylmethane structures, the glass transition temperature (Tg) of the compound (A1) itself is high, and the Tg value for the unprotected compound prior to protection with the acid dissociable, dissolution inhibiting groups is also high. Even if the purity of the compound is poor, the superiority of the Tg values can be retained, meaning the compound is particularly ideal as the base component (A) of a positive resist composition.

<Positive Resist Composition>

The positive resist composition of the present invention includes a base material component (A) that exhibits increased alkali solubility under the action of acid (hereafter referred to as "component (A)"), and an acid generator component (B) that generates acid upon irradiation (hereafter referred to as "component (B)"), wherein the component (A) includes the compound (A1).

In the positive resist composition including the component (A) and the component (B), when the acid generated from the component (B) upon exposure acts upon the component (A), the entire component (A) changes from an alkali-insoluble state to an alkali-soluble state. As a result, when a resist film formed from the positive resist composition is selectively exposed during resist pattern formation, or alternatively, is exposed and then subjected to post exposure baking, the exposed portions of the resist shift to an alkali-soluble state, whereas the unexposed portions remain insoluble in alkali, meaning alkali developing can then be used to form a positive resist pattern.

[Component (A)]

The component (A) includes the compound (A1).

As the compound (A1), either a single compound may be used alone, or two or more different compounds may be used in combination.

The proportion of the compound (A1) within the component (A) is preferably greater than 40% by weight, more preferably greater than 50% by weight, still more preferably greater than 80% by weight, and is most preferably 100% by weight.

The proportion of the compound (A1) within the component (A) can be measured using a technique such as reverse-phase chromatography.

The component (A) may also include any of the conventional resin components that have been proposed as base material components for chemically amplified resists (hereafter also referred to as "component (A2)"), provided the inclusion of these components does not impair the effects obtained by using the compound (A1).

Examples of the component (A2) include any of the materials proposed as base resins for conventional chemically amplified KrF positive resist compositions or ArF positive resist compositions or the like, and these can be selected in accordance with the type of exposure light source used during resist pattern formation.

The amount of the component (A) within the positive resist composition may be adjusted in accordance with the film thickness of the resist to be formed.

[Component (B)]

As the component (B), there is no particular limitation, and any of the known acid generators used in conventional chemically amplified resist compositions can be used.

Examples of these acid generators are numerous, and include onium salt-based acid generators such as iodonium salts and sulfonium salts, oxime sulfonate-based acid generators, diazomethane-based acid generators such as bisalkyl or bisaryl sulfonyl diazomethanes and poly(bis-sulfonyl)diazomethanes, nitrobenzylsulfonate-based acid generators, iminosulfonate-based acid generators, and disulfone-based acid generators.

Examples of onium salt-based acid generators include compounds represented by general formula (b-0) shown below.

[Chemical Formula 18]

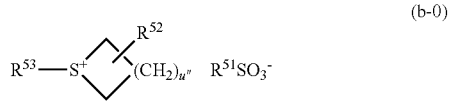

(b-0)

[wherein, $R^{51}$ represents a linear, branched or cyclic alkyl group, or a linear, branched or cyclic fluorinated alkyl group; $R^{52}$ represents a hydrogen atom, hydroxyl group, halogen atom, linear or branched alkyl group, linear or branched halogenated alkyl group, or linear or branched alkoxy group; $R^{53}$ represents an aryl group that may contain a substituent; and u" represents an integer of 1 to 3.]

In general formula (b-0), $R^{51}$ represents a linear, branched or cyclic alkyl group, or a linear, branched or cyclic fluorinated alkyl group.

The linear or branched alkyl group preferably contains 1 to 10 carbon atoms, more preferably 1 to 8 carbon atoms, and most preferably 1 to 4 carbon atoms.

The cyclic alkyl group preferably contains 4 to 12 carbon atoms, more preferably 5 to 10 carbon atoms, and most preferably 6 to 10 carbon atoms.

The fluorinated alkyl group preferably contains 1 to 10 carbon atoms, more preferably 1 to 8 carbon atoms, and most preferably 1 to 4 carbon atoms. Furthermore, the fluorination ratio within the fluorinated alkyl group (the ratio of the number of substituted fluorine atoms relative to the total number of hydrogen atoms within the alkyl group) is preferably within a range from 10 to 100% and more preferably from 50 to 100%, and groups in which all of the hydrogen atoms have been substituted with fluorine atoms are the most desirable as they yield the strongest acids.

As the group $R^{51}$, a linear alkyl group or fluorinated alkyl group is the most desirable.

$R^{52}$ represents a hydrogen atom, a hydroxyl group, a halogen atom, a linear, branched or cyclic alkyl group, a linear or branched halogenated alkyl group, or a linear or branched alkoxy group.

Examples of the halogen atom for $R^{12}$ include a fluorine atom, bromine atom, chlorine atom or iodine atom, and a fluorine atom is preferred.

The alkyl group for $R^{52}$ is preferably a linear or branched group, and the group preferably has 1 to 5 carbon atoms, more preferably 1 to 4 carbon atoms, and most preferably 1 to 3 carbon atoms.

Examples of the halogenated alkyl group for $R^{52}$ include groups in which some or all of the hydrogen atoms within the alkyl group have been substituted with halogen atoms. Here, an "alkyl group" refers to the same type of group as the "alkyl group" described above for $R^{52}$. Examples of the substituent halogen atoms include the same halogen atoms as those described above in relation to the "halogen atom" for the group $R^{52}$. In the halogenated alkyl group, 50 to 100% of the total number of hydrogen atoms are preferably substituted with halogen atoms, and groups in which all of the hydrogen atoms have been substituted are particularly desirable.

The alkoxy group for $R^{52}$ is a linear or branched group, and the group preferably has 1 to 5 carbon atoms, more preferably t to 4 carbon atoms, and most preferably 1 to 3 carbon atoms.

Of the groups described above, $R^{52}$ is most preferably a hydrogen atom.

$R^{53}$ represents an aryl group that may contain a substituent, and examples of the basic ring structure exclusive of any substituents (the parent ring) include a naphthyl group, phenyl group or anthracenyl group, and from the viewpoints of maximizing the effects of the present invention and ensuring favorable absorption of the exposure light from the ArF excimer laser or the like, a phenyl group is preferred.

Examples of the substituent include a hydroxyl group or a lower alkyl group (which may be linear or branched, preferably contains not more than 5 carbon atoms, and is most preferably a methyl group).

The aryl group for $R^{53}$ preferably contains no substituents.

u" represents an integer of 1 to 3, is preferably either 2 or 3, and is most preferably 3.

Examples of preferred acid generators represented by general formula (b-0) include compounds represented by the chemical formulas shown below.

[Chemical Formula 19]

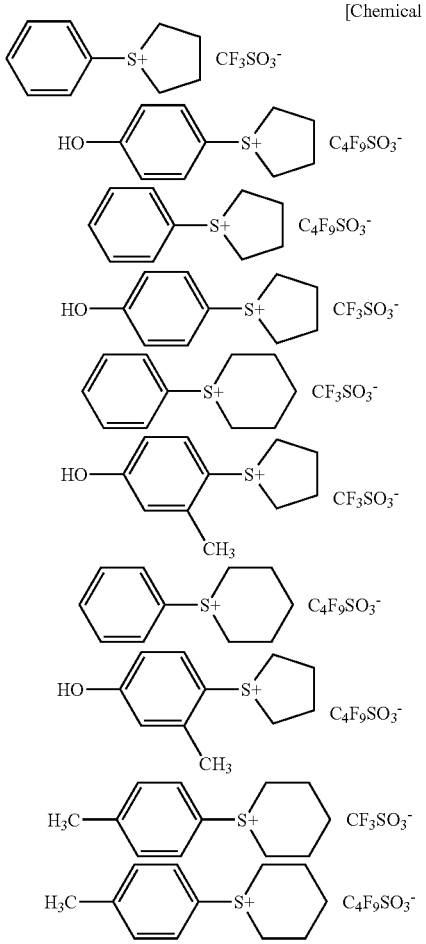

The acid generator represented by general formula (b-0) may be either a single type, or a mixture containing two or more different types.

Examples of onium salt-based acid generators besides those represented by general formula (b-0) include compounds represented by general formulas (b-1) and (b-2) shown below.

[Chemical Formula 20]

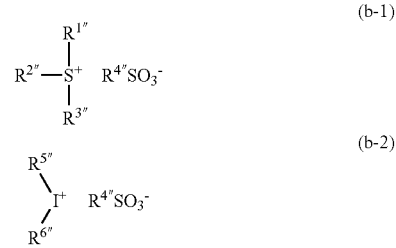

[wherein $R^{1\prime\prime}$ to $R^{3\prime\prime}$, $R^{5\prime\prime}$ and $R^{6\prime\prime}$ each independently represents an aryl group or alkyl group, and $R^{4\prime\prime}$ represents a linear, branched or cyclic alkyl group or fluorinated alkyl group, with the proviso that at least one of $R^{1\prime\prime}$ to $R^{3\prime\prime}$ represents an aryl group, and at least one of $R^{5\prime\prime}$ and $R^{6\prime\prime}$ represents an aryl group.

In formula (b-1), $R^{1\prime\prime}$ to $R^{3\prime\prime}$ each independently represents an aryl group or an alkyl group. Among $R^{1\prime\prime}$ to $R^{3\prime\prime}$, at least one group represents an aryl group. Among R¹" to R³", two or more groups are preferably aryl groups, and it is particularly desirable that all of R¹" to R³" are aryl groups.

The aryl group for R¹" to R³" is not specifically limited. For example, an aryl group having 6 to 20 carbon atoms may be used in which some or all of the hydrogen atoms of the aryl group may or may not be substituted with alkyl groups, alkoxy groups or halogen atoms. The aryl group is preferably an aryl group having 6 to 10 carbon atoms because it can be synthesized at a low cost. Specific examples thereof include a phenyl group and a naphthyl group.

The alkyl group with which hydrogen atoms of the aryl group may be substituted is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, and most preferably a methoxy group or an ethoxy group.

The halogen atom with which hydrogen atoms of the aryl group may be substituted is preferably a fluorine atom.

The alkyl group for R¹" to R³" is not specifically limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, ethyl group, n-propyl group, isopropyl group, n-butyl group, isobutyl group, n-pentyl group, cyclopentyl group, hexyl group, cyclohexyl group, nonyl group or decanyl group, and a methyl group is most preferable because it is excellent in resolution and can be synthesized at a low cost.

It is particularly desirable that all of R¹" to R³" are phenyl groups.

R⁴" represents a linear, branched or cyclic alkyl or fluorinated alkyl group.

The linear alkyl group preferably has 1 to 10 carbon atoms, more preferably 1 to 8 carbon atoms, and most preferably 1 to 4 carbon atoms.

The cyclic alkyl group is preferably a cyclic group as described for R¹", having 4 to 15 carbon atoms, more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms.

Further, the fluorination ratio of the fluorinated alkyl group (the ratio of fluorine atoms within the alkyl group) is preferably from 10 to 100%, and more preferably from 50 to 100%, and it is particularly desirable that all hydrogen atoms are substituted with fluorine atoms because the acid strength increases.

R⁴" is most preferably a linear or cyclic alkyl group or fluorinated alkyl group.

In formula (b-2), R⁵" and R⁶" each independently represents an aryl group or an alkyl group. At least one of R⁵" and R⁶" represents an aryl group. It is preferable that both of R⁵" and R⁶" represents an aryl group.

As the aryl group for R⁵" and R⁶", the same groups as the aryl groups for R¹" to R³" can be exemplified.

As the alkyl group for R⁵" and R⁶", the same groups as the alkyl groups for R¹" to R³" can be exemplified.

It is particularly desirable that both of R⁵" and R⁶" represents a phenyl group.

As R⁴" in formula (b-2), the same groups as those mentioned above for R⁴" in formula (b-1) can be exemplified.

Specific examples of the onium salt-based acid generators represented by formulas (b-1) and (b-2) include diphenyliodonium trifluoromethanesulfonate or nonafluorobutanesulfonate, bis(4-tert-butylphenyl)iodonium trifluoromethanesulfonate or nonafluorobutanesulfonate, triphenylsulfonium trifluoromethanesulfonate, heptafluoropropanesulfonate or nonafluorobutanesulfonate, tri(4-methylphenyl)sulfonium trifluoromethanesulfonate, heptafluoropropanesulfonate or nonafluorobutanesulfonate, dimethyl(4-hydroxynaphthyl)sulfonium trifluoromethanesulfonate, heptafluoropropanesulfonate or nonafluorobutanesulfonate, monophenyldimethylsulfonium trifluoromethanesulfonate, heptafluoropropanesulfonate or nonafluorobutanesulfonate, diphenylmonomethylsulfonium trifluoromethanesulfonate, heptafluoropropanesulfonate or nonafluorobutanesulfonate, (4-methylphenyl)diphenylsulfonium trifluoromethanesulfonate, heptafluoropropanesulfonate or nonafluorobutanesulfonate, (4-methoxyphenyl)diphenylsulfonium trifluoromethanesulfonate, heptafluoropropanesulfonate or nonafluorobutanesulfonate, tri(4-tert-butyl)phenylsulfonium trifluoromethanesulfonate, heptafluoropropanesulfonate or nonafluorobutanesulfonate, and diphenyl(1-(4-methoxy)naphthyl)sulfonium trifluoromethanesulfonate, heptafluoropropanesulfonate or nonafluorobutanesulfonate. It is also possible to use onium salts in which the anion moiety of these onium salts are replaced by methanesulfonate, n-propanesulfonate, n-butanesulfonate, or n-octanesulfonate.

Further, onium salt-based acid generators in which the anion moiety in general formula (b-1) or (b-2) is replaced with an anion moiety represented by general formula (b-3) or (b-4) shown below (the cation moiety is the same as (b-1) or (b-2)) may also be used.

[Chemical Formula 21]

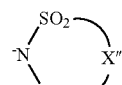
(b-3)

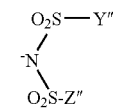
(b-4)

[wherein, X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.]

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Y" and Z" each independently represents a linear or branched alkyl group in which at least one hydrogen atom has been substituted with a fluorine atom, and the alkyl group has 1 to 10 carbon atoms, preferably 1 to 7 carbon atoms, and more preferably 1 to 3 carbon atoms.

The smaller the number of carbon atoms of the alkylene group of X" or carbon atoms of the alkyl group of Y" and Z" within the above range for the number of carbon atoms, the more the solubility in a resist solvent improves.

Further, in the alkylene group of X" or the alkyl group of Y" and Z", it is preferable that the number of hydrogen atoms substituted with a fluorine atom is as large as possible, as the acid strength increases, and the transparency to high energy radiation of 200 nm or less or an electron beam is improved. The fluorination ratio the alkylene group or alkyl group is preferably from 70 to 100% and more preferably from 90 to 100%, and it is particularly desirable that the alkylene group or alkyl group a perfluoroalkylene or perfluoroalkyl group in which all hydrogen atoms are substituted with fluorine atoms.

In the present description, an oxime sulfonate-based acid generator refers to a compound having at least one group represented by general formula (B-1) shown below, and has a feature of generating acid by irradiation. Such oxime sulfonate-based acid generators are widely used for chemically amplified resist compositions, and can be appropriately selected.

[Chemical Formula 22]

(B - 1)

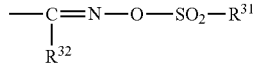

[wherein $R^{31}$ and $R^{32}$ each independently represents an organic group.]

The "organic group" for $R^{31}$ and $R^{32}$ refers to a group that contains a carbon atom, and may also include atoms other than the carbon atom (such as a hydrogen atom, an oxygen atom, a nitrogen atom, a sulfur atom, or a halogen atom (such as a fluorine atom and a chlorine atom)).

As the organic group for $R^{31}$, a linear, branched, or cyclic alkyl group or aryl group is preferable. The alkyl group or the aryl group may have a substituent. The substituent is not particularly limited, and examples thereof include a fluorine atom or a linear, branched or cyclic alkyl group having 1 to 6 carbon atoms. The expression "have a substituent" means that some or all of the hydrogen atoms of the alkyl group or the aryl group are replaced with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, chlorine atom, bromine atom or iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, a partially or completely halogenated aryl group is particularly desirable.

The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^1$, an alkyl group of 1 to 4 carbon atoms that has no substituent or a fluorinated alkyl group of 1 to 4 carbon atoms is particularly desirable.

As the organic group for $R^{32}$, a linear, branched or cyclic alkyl group, an aryl group, or a cyano group is preferable. Examples of the alkyl group and the aryl group for $R^{32}$ are the same as those of the alkyl group and the aryl group for $R^{31}$.

As $R^{32}$, a cyano group, an alkyl group of 1 to 8 carbon atoms having no substituent, or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 23]

(B - 2)

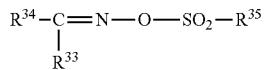

[wherein, $R^{33}$ represents a cyano group, an alkyl group having no substituent or a halogenated alkyl group, $R^{34}$ represents an aryl group, and $R^{35}$ represents an alkyl group having no substituent or a halogenated alkyl group.]

[Chemical Formula 24]

(B-3)

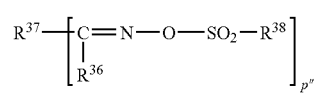

[wherein, $R^{36}$ represents a cyano group, an alkyl group having no substituent or a halogenated alkyl group, $R^{37}$ represents a divalent or trivalent aromatic hydrocarbon group, $R^{38}$ represents an alkyl group having no substituent or a halogenated alkyl group, and p" represents 2 or 3.]

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and still more preferably 90% or more.

Examples of the aryl group for $R^{34}$ include groups in which one hydrogen atom has been removed from an aromatic hydrocarbon ring, such as a phenyl group, biphenyl group, fluorenyl group, naphthyl group, anthracyl group or phenanthryl group, as well as heteroaryl groups in which some of the carbon atoms constituting the ring(s) of these groups are substituted with hetero atoms such as an oxygen atom, a sulfur atom or a nitrogen atom. Of these, a fluorenyl group is preferable.

The aryl group for $R^{34}$ may have a substituent such as an alkyl group of 1 to 10 carbon atoms, a halogenated alkyl group or an alkoxy group. The alkyl group or the halogenated alkyl group serving as the substituent preferably has 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the alkyl group hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), the alkyl group having no substituent and the halogenated alkyl group for $R^{36}$ are the same as the alkyl group having no substituent and the halogenated alkyl group for $R^{33}$.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same groups as the alkyl group having no substituent or the halogenated alkyl group for $R^{35}$ may be exemplified.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p methoxyphenyl acetonitrile, α-(trifluoromethylsulfonyloxyimino) phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 ([Chemical Formula 18] and [Chemical Formula 19] shown in paragraphs [0012] to [0014]) and oxime sulfonate-based acid generators disclosed in WO 20041074242A2 (Examples 1 to 40 described on pages 65 to 85) may be used favorably.

Furthermore, preferred examples include the compounds shown below.

[Chemical Formula 25]

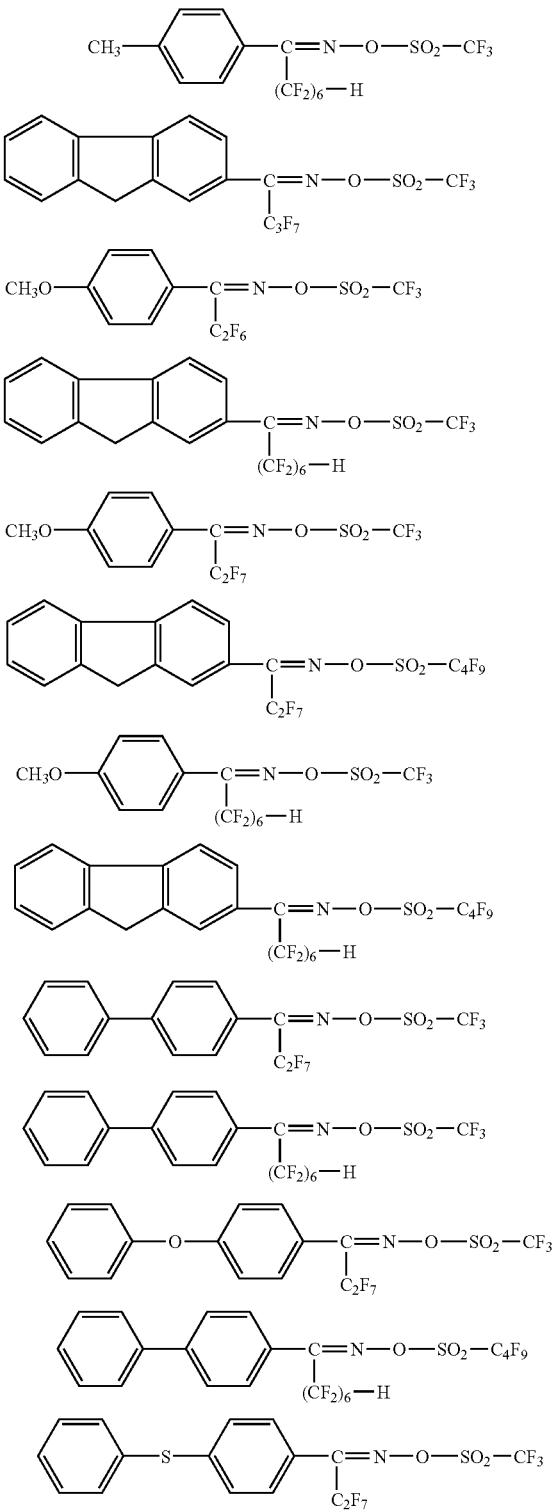

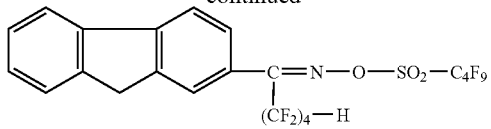

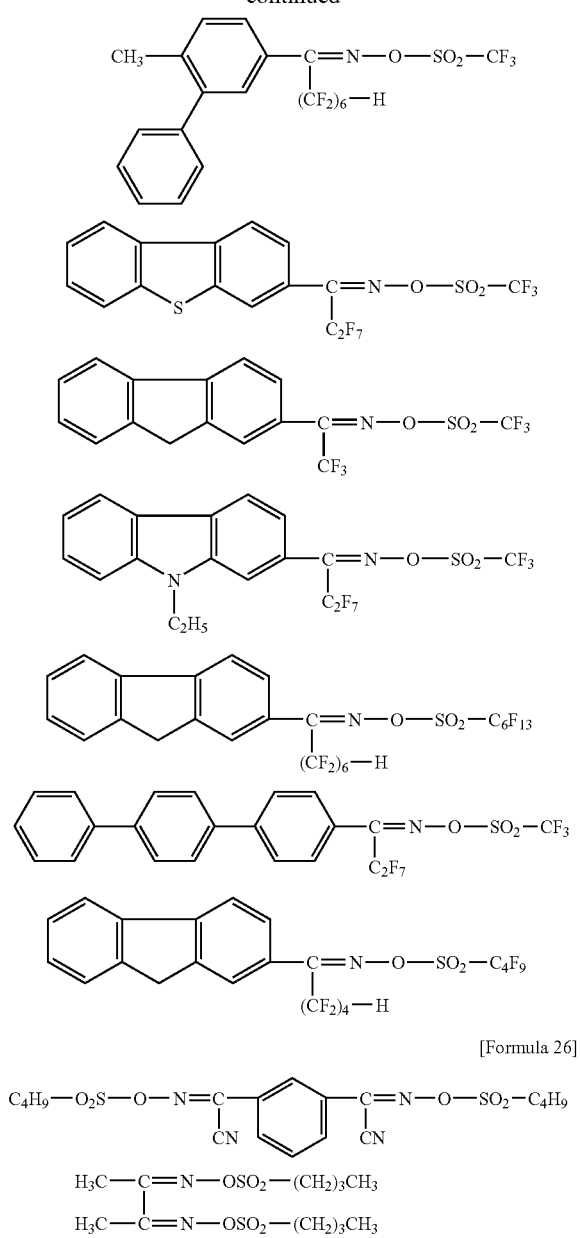

Among the above-exemplified compounds, the following four compounds are particularly desirable.

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may also be used favorably.

Furthermore, specific examples of poly(bis-sulfonyl)diazomethanes include those disclosed in Japanese Unexamined Patent Application, First Publication No. Hei 11-322707, including 1,3-bisphenylsulfonyldiazomethylsulfonyl)propane, 1,4-bis(phenylsulfonyldiazomeThylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane.

As the component (B), one type of acid generator may be used alone, or two or more different acid generators may be used in combination.

The amount of the component (B) is preferably from 0.5 to 30 parts by weight, and more preferably 1 to 15 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

[Optional Components]

In the positive resist composition, for improving the resist pattern shape and the post exposure stability of the latent image formed by the pattern-wise exposure of the resist layer, it is preferable to add a nitrogen-containing organic compound (D) (hereafter referred to as "component (D)") as an optional component.

A multitude of these components (D) have already been proposed, and any of these known compounds may be used, including monoalkylamines such as n-hexylamine, n-heptylamine, n-octylamine, n-nonylamine and n-decylamine; dialkylamines such as diethylamine, di-n-propylamine, di-n-heptylamine, di-n-octylamine and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine; and alkyl alcohol amines such as diethanolamine, triethanolamine, diisopropanolamine, triisopropanolamine, di-n-octanolamine, and tri-n-octanolamine. Among these, secondary aliphatic amines and tertiary aliphatic amines are preferred, trialkylamines of 5 to 10 carbon atoms are more preferred, and tri-n-octylamine is the most desirable.

These compounds can be used either alone, or in combinations of two or more different compounds.

The component (D) is typically used in an amount within a range from 0.01 to 5.0 parts by weight, relative to 100 parts by weight of the component (A).

Furthermore, in the positive resist composition, for preventing any deterioration in sensitivity caused by the addition of the above component (D), and improving the resist pattern shape and the post exposure stability of the latent image formed by the pattern-wise exposure of the resist layer, an organic carboxylic acid, or a phosphorus oxo acid or derivative thereof (E) (hereafter referred to as "component (E)") can also be added as another optional component. The component (D) and the component (E) can be used in combination, or either one can also be used alone.

Examples of suitable organic carboxylic acids include malonic acid, citric acid, malic acid, succinic acid, benzoic acid, and salicylic acid.

Examples of suitable phosphorus oxo acids or derivatives thereof include phosphoric acid or derivatives thereof such as esters, including phosphoric acid, di-n-butyl phosphate and diphenyl phosphate; phosphonic acid or derivatives thereof such as esters, including phosphonic acid, dimethyl phosphonate, di-n-butyl phosphonate, phenylphosphonic acid, diphenyl phosphonate, and dibenzyl phosphonate; and phosphinic acid or derivatives thereof such as esters, including phosphinic acid and phenylphosphinic acid, and of these, phosphonic acid is particularly desirable.

The component (E) is typically used in an amount within a range from 0.01 to 5.0 parts by weight, relative to 100 parts by weight of the component (A).

If desired, other miscible additives can also be added to the positive resist composition. Examples of such miscible additives include additive resins for improving the performance of the resist film, surfactants for improving the applicability, dissolution inhibitors, plasticizers, stabilizers, colorants, halation prevention agents, and dyes.

The positive resist composition can be prepared by dissolving the materials for the resist composition in an organic solvent (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl n-amyl ketone, methyl isoamyl ketone and 2-heptanone; polyhydric alcohols and derivatives thereof such as ethylene glycol, diethylene glycol, propylene glycol and dipropylene glycol; polyhydric alcohol derivatives, including compounds having an ester bond such as ethylene glycol monoacetate, diethylene glycol monoacetate, propylene glycol monoacetate and dipropylene glycol monoacetate, and compounds having an ether bond, including monoalkyl ethers (such as a monomethyl ether, monoethyl ether, monopropyl ether or monobutyl ether) or a monophenyl ether of any of the above polyhydric alcohols or compounds having an ester bond; cyclic ethers such as dioxane; esters such as methyl lactate, ethyl lactate (EL), methyl acetate, ethyl acetate, butyl acetate, methyl pyruvate, ethyl pyruvate, methyl methoxypropionate and ethyl ethoxypropionate; and aromatic organic solvents such as anisole, ethyl benzyl ether, cresyl methyl ether, diphenyl ether, dibenzyl ether, phenetole, butyl phenyl ether, ethylbenzene, diethylbenzene, amylbenzene, isopropylbenzene, toluene, xylene, cymene and mesitylene.

These solvents may be used individually, or in combination as a mixed solvent.

Among these solvents, propylene glycol monomethyl ether acetate (PGMEA), propylene glycol monomethyl ether (PGME) and EL are preferred.

Further, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably from 1:9 to 9:1, and more preferably from 2:8 to 8:2.

Specifically, when EL is mixed as the polar solvent the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably from 3:7 to 7:3.

Further, a mixed solvent of at least one of PGMEA and EL with γ-butyrolactone is also preferred as the component (S). The mixing ratio (former: latter) of such a mixed solvent is preferably from 70:30 to 95:5.

The amount used of the component (S) is not particularly limited, and is appropriately adjusted to a concentration that enables coating of a coating solution to a substrate in accordance with the thickness of the coating film. In general, the organic solvent is used in an amount that yields a solid content for the resist composition that is within the range from 2 to 20% by weight, and preferably from 5 to 15% by weight.

<Method for Forming a Resist Pattern>

The positive resist composition can be used within a method for forming a resist pattern that includes: forming a resist film on a substrate using the positive resist composition, exposing the resist film, and developing the resist film to form a resist pattern.

The method for forming the resist pattern can be performed, for example, as follows. Firstly, the positive resist composition is applied onto a substrate such as a silicon wafer using a spinner or the like, and an optional prebake (PAB) is conducted to form a resist film. Following selective exposure of the formed resist film, either by exposure through a mask pattern using an exposure apparatus such as an ArF exposure apparatus, an electron beam lithography apparatus or an EUV exposure apparatus, or by patterning via direct irradiation with an electron beam without using a mask pattern, PEB (post exposure baking) is conducted. Subsequently, developing is conducted using an alkali developing solution, a rinse treatment is performed to wash away the residual developing solution on the substrate and the portions of the resist composition that have been dissolved by the developing solution, and the resist is then dried, yielding a resist pattern.

These steps can be conducted using conventional techniques. The operating conditions and the like are preferably set in accordance with factors such as the formulation and properties of the positive resist composition being used.

There are no particular limitations on the exposure source, and radiations such as an ArF excimer laser, KrF excimer laser, $F_2$ excimer laser, EUV (Extreme Ultra Violet), VUV (Vacuum Ultra Violet), electron beam, X-ray or soft X-ray radiation can be used. The positive resist composition described above is particularly effective for use with an ArF excimer laser, an electron beam or EUW radiation, and an ArF excimer laser or electron beam is particularly desirable.

In some cases, the method may also include a post bake step following the above alkali developing step, and an organic or inorganic antireflection film may also be provided between the substrate and the resist film.

<Dissolution Inhibitor>

The compound (A1) described above can also be used favorably as a dissolution inhibitor for a positive resist composition. By using a dissolution inhibitor formed from the compound (A1), the alkali solubility (prior to exposure) of the resist film obtained using the positive resist composition containing the dissolution inhibitor is inhibited. As a result, when the resist film is selectively exposed, the difference in alkali solubility between the exposed portions and the unexposed portions (the solubility contrast) increases, and a resist pattern with favorable resolution and shape can be formed.

This dissolution inhibitor can be used by adding the dissolution inhibitor to a two-component chemically amplified resist composition including a resin component having acid dissociable, dissolution inhibiting groups, and an acid generator component. Furthermore, the dissolution inhibitor may also be used in a so-called three-component chemically amplified resist composition, which includes a resin component having no acid dissociable, dissolution inhibiting groups, an acid generator component, and the dissolution inhibitor.

EXAMPLES

As follows is a description of examples of the present invention, although the scope of the present invention is in no way limited by these examples.

Synthesis Example 1

(i) Synthesis of TRIFTOCPA-TCM (Compound (1))

To 27.5 g (0.05 mols) of TRIF-TOCPA (see formula below) was added 68.8 g of N-methylpyrrolidone, and the mixture was dissolved. The temperature of the solution was raised to 50° C., 2.75 g (0.017 mols) of potassium iodide and 24.2 g (0.175 mols) of potassium carbonate were added, and the resulting mixture was stirred for one hour. Subsequently, the temperature was raised to 70° C., 32.6 g (0.3 mols) of methyl chloroacetate was added dropwise over one hour, and the resulting mixture was then stirred for 6 hours at 70° C. Subsequently, 100.0 g of water and 120.0 g of toluene were added, and following water washing at 60° C., the water layer was removed. By adding additional 50.0 g samples of water, the operation of washing with water and separating the phases was conducted three times. The remaining upper layer was transferred to a round-bottom flask, and the solvent was removed by evaporation at 70° C. using an evaporator, yielding 40.5 g of a brown liquid of the compound (1) TRIFTOCPA-TCM. The product purity was 92.8% (HPLC).

[Chemical Formula 28]

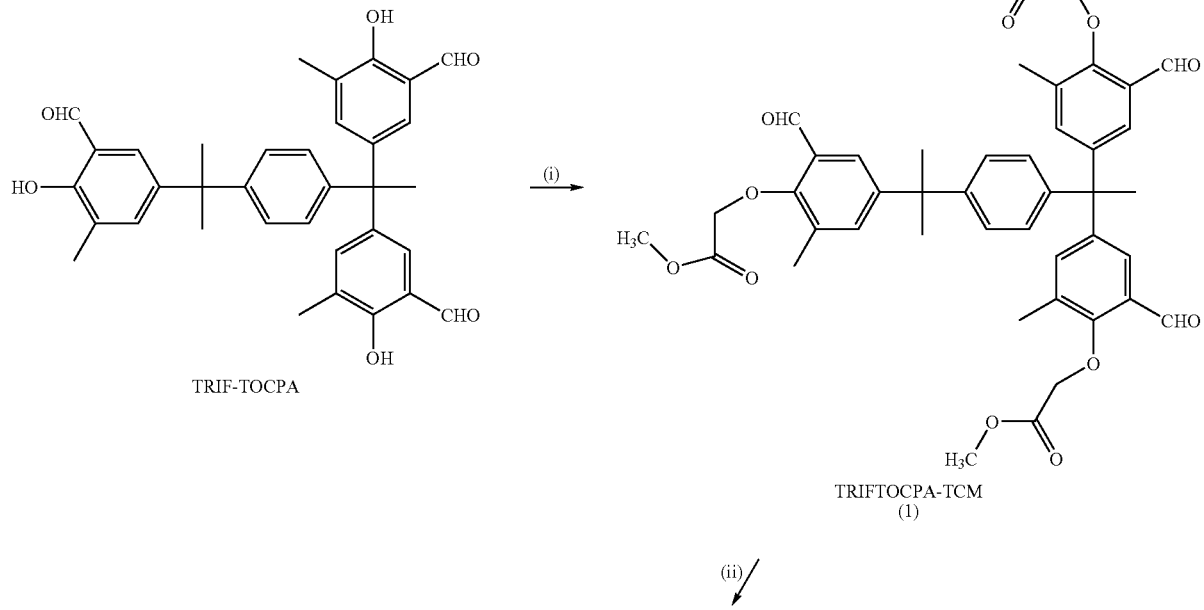

-continued
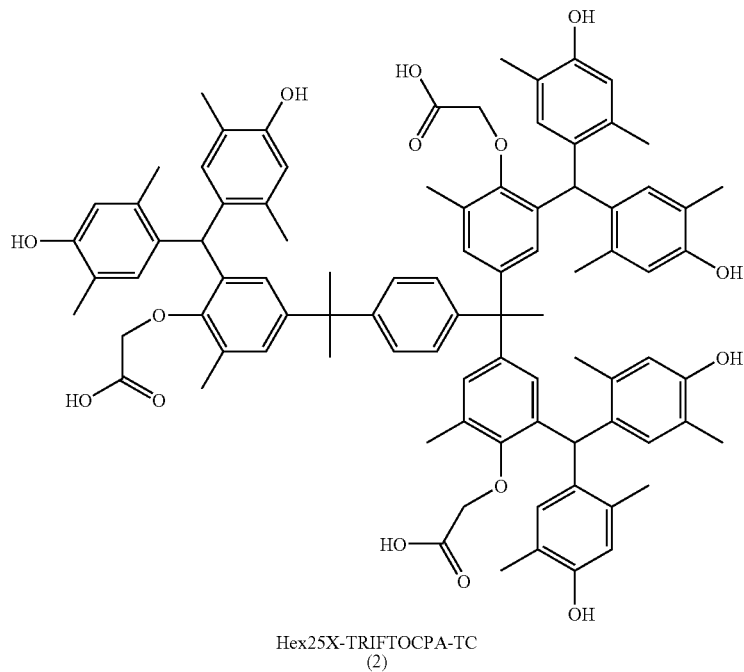
Hex25X-TRIFTOCPA-TC
(2)
↓(iii)
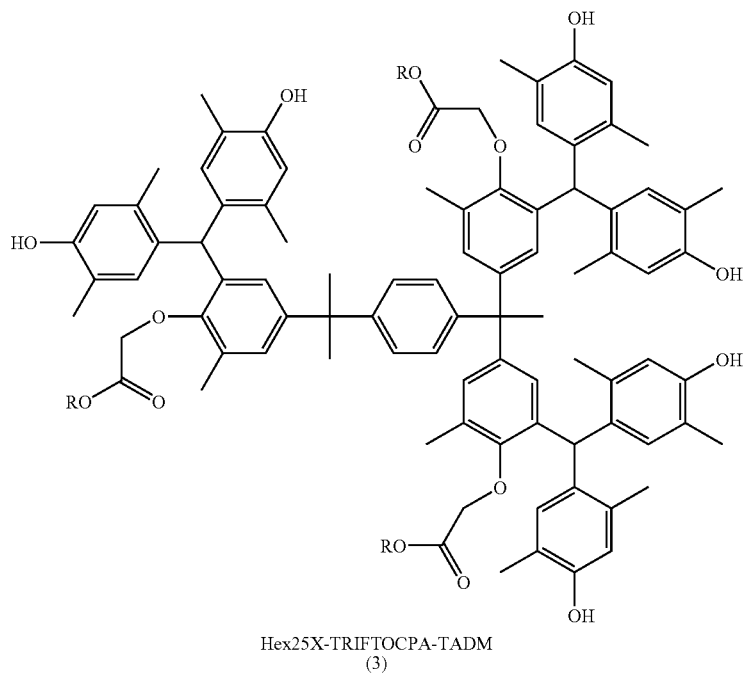
Hex25X-TRIFTOCPA-TADM
(3)
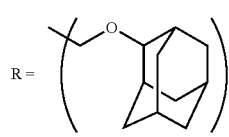

(ii) Synthesis of Hex25X-TRIFTOCPA-TC (Compound (2))

Subsequently, a solution prepared by mixing the 40.5 g of brown liquid (TRIFTOCPA-TCM) obtained in (i) above with 45.0 g of tetrahydrofuran was added dropwise at 30° C. over one hour and 30 minutes to a mixed solution composed of 45.8 g (0.375 mols) of 2,5-xylenol, 55.0 g of methanol and 9.2 g of a 35% aqueous solution of hydrochloric acid. Following completion of the addition, the temperature was raised to 40° C., the reaction mixture was stirred for 22.5 hours, and 23.1 g of a 16% aqueous solution of sodium hydroxide was then added to neutralize the reaction solution. The solution was then concentrated at normal pressure to remove 115.9 g of solvent by evaporation, 80.0 g of water and 120.0 g of methyl isobutyl ketone were added, the temperature was raised to 70° C., and then following standing for 10 minutes, the water layer was removed. An additional 80.0 g of water was added, and the same operation of washing with water and separating the phases was repeated. Subsequently, 98.4 g of a 25% aqueous solution of TMAH was added, the mixture was stirred at 40° C. for 30 minutes to effect hydrolysis, and the upper layer was removed. To the remaining water layer at 40° C. were added 120.0 g of methyl isobutyl ketone and 180.0 g of a 17.5% aqueous solution of hydrochloric acid, the water layer was removed, an additional 80.0 g of water was added, and the same operation of washing with water and separating the phases was conducted at 70° C. The remaining upper layer was transferred to a round-bottom flask, and the solvent was removed by evaporation at 70° C. using an evaporator, yielding 37.3 g of a pale yellow powder (Hex25X-TRIFTOCPA-TC). The product Tg value was 159° C., and the purity was 87.7% (HPLC).

Example 1

(iii) Synthesis of Hex25X-TRIFTOCPA-TADM (Compound (3))

28.0 g ($2.0 \times 10^{-2}$ mols) of the Hex25X-TRIFTOCPA-TC obtained in (ii) above was mixed with 112.0 g of tetrahydrofuran, and a mixed solution composed of 7.6 g ($7.5 \times 10^{-2}$ mols) of triethylamine and 28.0 g of tetrahydrofuran was added dropwise to the resulting mixture at 25° C. over a period of 15 minutes. The resulting mixture was then stirred for one hour. A mixed solution composed of 14.0 g ($7.0 \times 10^{-2}$ mols) of 2-chloromethoxyadamantane and 14.0 g of tetrahydrofuran was then added dropwise to the reaction mixture at 30° C. over a period of one hour and 40 minutes. Subsequently, stirring was continued for 5 hours with the temperature maintained at 30° C., and 116.4 g of solvent was then removed by evaporation under reduced pressure. To the resulting residue were added 80.0 g of ethyl acetate and 40.0 g of water, and following water washing at 40° C., a separation was conducted to remove the lower layer. The same operation of washing with water and conducting a separation was repeated twice. The remaining upper layer was then concentrated under reduced pressure and purified by silica gel column chromatography. The fraction containing the target product was concentrated, yielding 3.6 g of a pale yellowish white powder. The purity was 99.0% (HPLC).

The compound (3) was analyzed using $^1$H-NMR and IR.

$^1$H-NMR (deuterated dimethylsulfoxide (DMSO-d6), 400 MHz, internal standard: tetramethylsilane): δ (ppm)=1.41 to 2.07 (m, 96H, —CH$_3$ ((1)+(2)+(3)+(4)+(5)+(—CH$_2$—CH (except for ADM:(6))), 3.72 (s, 3H, —CH (ADM:(6))), 3.93 to 3.96 (m, 6H, —CH$_2$ (7)), 5.34 to 5.38 (m, 6H, —CH$_2$ (8)), 5.73 to 5.80 (m, 3H, —CH (9)), 6.19 to 7.05 (m, 22H, ph-H), 8.88 to 8.93 (m, 6H, ph-OH (2,5-xylenol)).

IR data (cm$^{-1}$): 3675, 2907, 2855.

Moreover, the result of an LC-MS (APCI$^-$) mass analysis revealed a molecular weight of 1895 (M-H). These results confirmed that the compound (3) had the structure shown below.

[Chemical Formula 29]

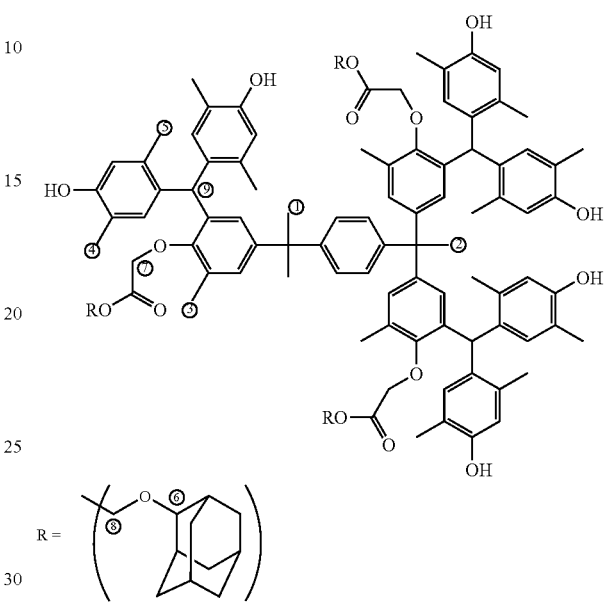

Example 2

A positive resist composition solution was prepared by dissolving 100 parts by weight of the compound (3) synthesized in Example 1, 10 parts by weight of triphenylsulfonium nonafluoro-n-butanesulfonate, and 1 part by weight of tri-n-octylamine in a mixed solvent (1470 parts by weight) in which PGMEA:EL=6:4.

The resulting positive resist composition solution was applied uniformly, using a spinner, to the surface of an 8-inch silicon substrate that had been treated with hexamethyldisilazane, and was then subjected to a bake treatment (PAB) at 11° C. for 90 seconds, thus forming a resist film (film thickness: 150 nm).

This resist film was then subjected to direct patterning (exposure) with an electron beam lithography apparatus HL-800D (VSB) (manufactured by Hitachi Ltd.) at an accelerating voltage of 70 kV, and was then subjected to a bake treatment (PEB) at 100° C. for 90 seconds, developed for 60 seconds in a 2.38% by weight aqueous solution of tetramethylammonium hydroxide (TMAH) (at 23° C.), and rinsed in pure water for 30 seconds, thus forming a line and space (L/S) pattern. As a result, a 120 nm L/S pattern (1:1) was able to be formed. Determination of the exposure dose (μC/cm$^2$) revealed a result of 48 μC/cm$^2$.

The above results confirmed that by using a positive resist composition that employed the compound of the present invention, a very fine resist pattern could be formed.

INDUSTRIAL APPLICABILITY

The present invention provides a novel compound that can be used for a resist composition, a positive resist composition that includes the compound, and a method for forming a resist pattern that uses the positive resist composition, and is therefore extremely useful industrially.

The invention claimed is:
1. A compound represented by a general formula (A-1) shown below:

[Formula 1]

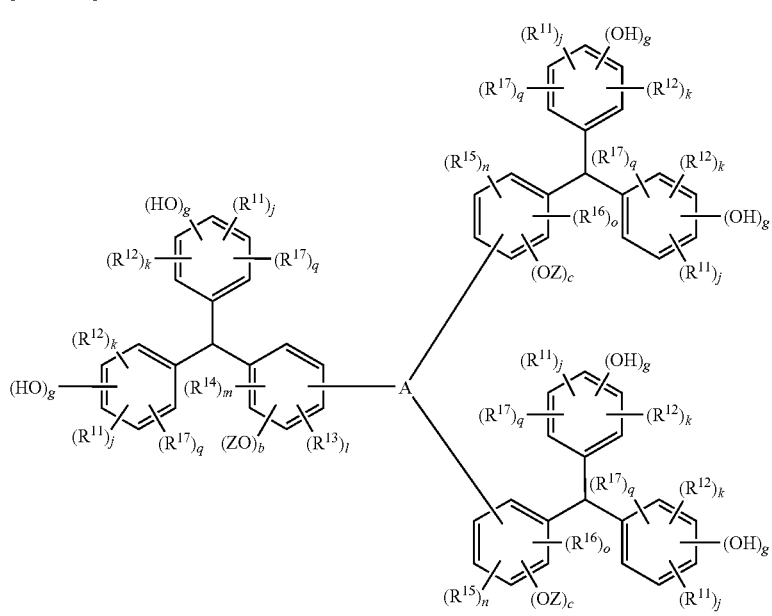

(A-1)

[wherein, $R^{11}$ to $R^{17}$ each independently represents an alkyl group or an aromatic hydrocarbon group of 1 to 10 carbon atoms, which may include a hetero atom within a structure thereof; g and j each independently represents an integer of 1 or greater, and k and q each represents an integer of 0 or greater, provided that g+j+k+q is not greater than 5; b represents an integer of 1 or greater, and l and m each independently represents an integer of 0 or greater, provided that b+l+m is not greater than 4; c represents an integer of 1 or greater, and n and o each independently represents an integer of 0 or greater, provided that c+n+o is not greater than 4; A represents a trivalent aromatic cyclic group, a trivalent alkyl group, a trivalent aliphatic cyclic group, or a trivalent organic group having an aromatic cyclic group or an aliphatic cyclic group; and Z represents a group represented by a general formula (z1) shown below:

[Chemical Formula 2]

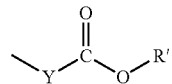

(z1)

(wherein, Y represents an alkylene group, a divalent aromatic hydrocarbon group, a divalent aliphatic cyclic group, or a divalent organic group having an aromatic hydrocarbon group or an aliphatic cyclic group; and R' represents an acid dissociable, dissolution inhibiting group)].

2. A compound according to claim 1, represented by a general formula (A-2) shown below:

[Chemical Formula 3]

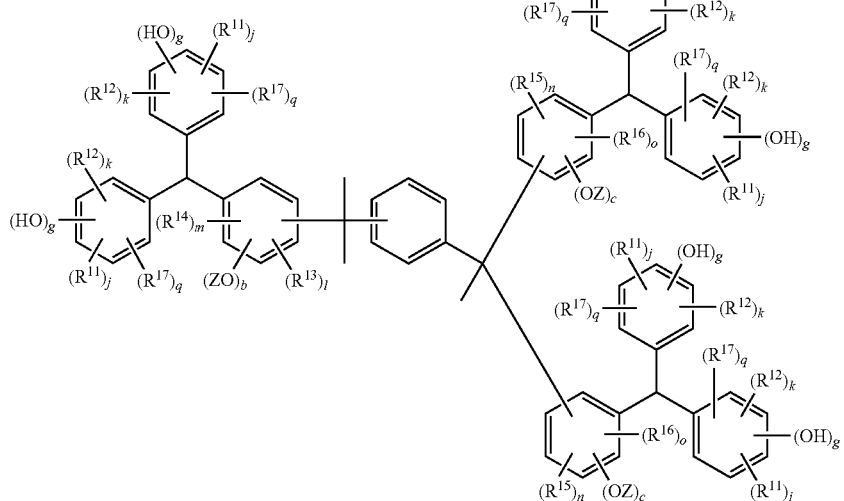

(A-1-1)

[wherein, $R^{11}$ to $R^{17}$ each independently represents an alkyl group of 1 to 10 carbon atoms or an aromatic hydrocarbon group, which may include a hetero atom within a structure thereof; g and j each independently represents an integer of 1 or greater, and k and q each represents an integer of 0 or greater, provided that g+j+k+q is not greater than 5; b represents an integer of 1 or greater, and l and m each independently represents an integer of 0 or greater, provided that b+l+m is not greater than 4; c represents an integer of 1 or greater, and n and o each independently represents an integer of 0 or greater, provided that c+n+o is not greater than 4; and Z is as defined above].

3. A positive resist composition comprising a base material component (A) that exhibits increased alkali solubility under action of acid, and an acid generator component (B) that generates acid upon irradiation, wherein
said base material component (A) comprises a compound (A1) represented by a general formula (A-1) shown below:

[Chemical Formula 4]

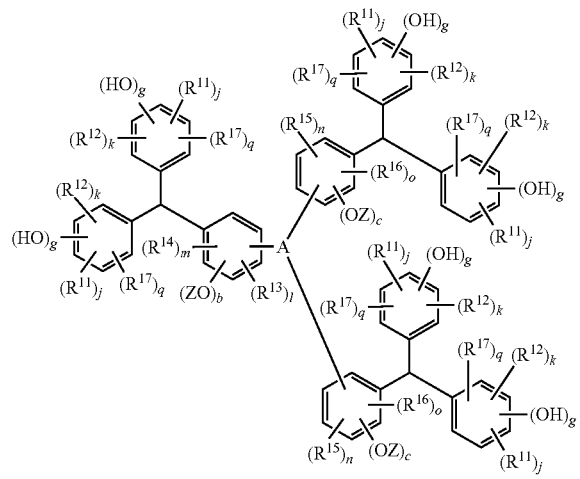

(A-1)

[wherein, $R^{11}$ to $R^{17}$ each independently represents an alkyl group or an aromatic hydrocarbon group of 1 to 10 carbon atoms, which may include a hetero atom within a structure thereof; g and j each independently represents an integer of 1 or greater, and k and q each represents an integer of 0 or greater, provided that g+j+k+q is not greater than 5; b represents an integer of 1 or greater, and l and m each independently represents an integer of 0 or greater, provided that b+l+m is not greater than 4; c represents an integer of 1 or greater, and n and o each independently represents an integer of 0 or greater, provided that c+n+o is not greater than 4; A represents a trivalent aromatic cyclic group, a trivalent alkyl group, a trivalent aliphatic cyclic group, or a trivalent organic group having an aromatic cyclic group or an aliphatic cyclic group; and Z represents a group represented by a general formula (z1) shown below:

[Chemical Formula 5]

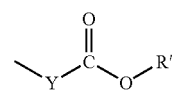

(z1)

(wherein, Y represents an alkylene group, a divalent aromatic hydrocarbon group, a divalent aliphatic cyclic group, or a divalent organic group having an aromatic hydrocarbon group or an aliphatic cyclic group; and R' represents an acid dissociable, dissolution inhibiting group)].

4. A positive resist composition according to claim 3, wherein said compound (A1) is a compound represented by a general formula (A-1-1) shown below:

[Chemical Formula 6]

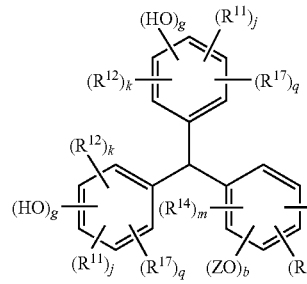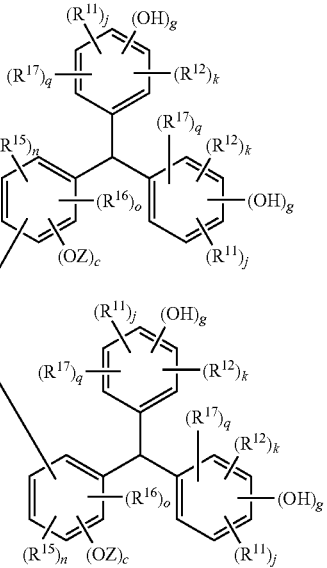

(A-1-1)

[wherein, $R^{11}$ to $R^{17}$ each independently represents an alkyl group of 1 to 10 carbon atoms or an aromatic hydrocarbon group, which may include a hetero atom within a structure thereof; g and j each independently represents an integer of 1 or greater, and k and q each represents an integer of 0 or greater, provided that g+j+k+q is not greater than 5; b represents an integer of 1 or greater, and l and m each independently represents an integer of 0 or greater, provided that b+l+m is not greater than 4; c represents an integer of 1 or greater, and n and o each independently represents an integer of 0 or greater, provided that c+n+o is not greater than 4; and Z is as defined above].

5. A positive resist composition according to claim 3, further comprising a nitrogen-containing organic compound (D).

6. A method for forming a resist pattern comprising: forming a resist film on a substrate using a positive resist composition according to claim 3, exposing said resist film, and developing said resist film to form a resist pattern.

* * * * *

UNITED STATES PATENT AND TRADEMARK OFFICE
CERTIFICATE OF CORRECTION

PATENT NO. : 8,017,300 B2
APPLICATION NO. : 12/299371
DATED : September 13, 2011
INVENTOR(S) : Daiju Shiono, Taku Hirayama and Hideo Hada It is certified that error appears in the above-identified patent and that said Letters Patent is hereby corrected as shown below:

At Column 2, Line 36 (Approx.), After "435" insert --.--.

At Column 3, Line 66-67, Delete "the base material component (A) contains a compound (A1) represented by general formula (A-1) shown below." and insert the same after "wherein" on Col. 3, Line 64 as a continuation of the paragraph.

At Column 7, Line 19, Change "R'" to --$R^1$--.

At Column 12, Line 47, Change "0.1+m" to --0. 1+m--.

At Column 14, Line 36 (Approx.), Change "invention" to --invention,--.

At Column 15, Line 25 (Approx.), Change "$R^1$," to --$R^{11}$,--.

At Column 20, Line 13, Change "trifluoromethanesulforic" to --trifluoromethanesulfonic--.

At Column 23, Line 25 (Approx.), Change "$R^{12}$" to --$R^{52}$--.

At Column 23, Line 46 (Approx.), Change "t" to --1--.

At Column 24, Line 20 (Structure),

Change " 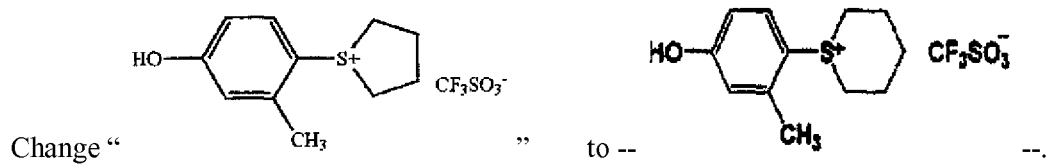 " to -- --.

Signed and Sealed this
Thirteenth Day of March, 2012

David J. Kappos
*Director of the United States Patent and Trademark Office*

At Column 24, Line 27 (Structure),

Change " 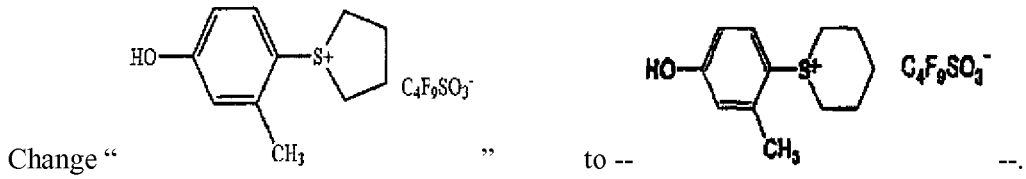 --.

At Column 24, Line 65, Change "group." to --group.]--.

At Column 28, Line 1, Change "$R^1$," to --$R^{31}$,--.

At Column 30, Line 2, Change "20041074242A2" to --2004/074242A2--.

At Column 31, Line 54 (Approx.), Change "$27^6$" to --27]--.

At Column 32, Line 25, Change "1,3-bisphenylsulfonyl" to --1,3-bis(phenylsulfonyl--.

At Column 32, Line 26, Change "Thylsulfonyl)" to --thylsulfonyl)--.

At Column 34, Line 21, Change "solvent" to --solvent,--.

At Column 34, Line 29 (Approx.), Change "(former: latter)" to --(former:latter)--.

At Column 35, Line 7 (Approx.), Change "EUW" to --EUV--.

At Column 40, Line 45, Change "11° C." to --110° C.--.